US010745463B2

(12) United States Patent
Sundberg et al.

(10) Patent No.: US 10,745,463 B2
(45) Date of Patent: Aug. 18, 2020

(54) HYPER-GLYCOSYLATED ANTIBODIES WITH SELECTIVE FC RECEPTOR BINDING

(71) Applicants: Eric J. Sundberg, Baltimore, MD (US); Beatriz Trastoy Bello, Bilbao (ES)

(72) Inventors: Eric J. Sundberg, Baltimore, MD (US); Beatriz Trastoy Bello, Bilbao (ES)

(73) Assignee: UNIVERSITY OF MARYLAND, BALTIMORE, Baltimore, MD (US)

( * ) Notice: Subject to any disclaimer, the term of this patent is extended or adjusted under 35 U.S.C. 154(b) by 383 days.

(21) Appl. No.: 15/037,185

(22) PCT Filed: Nov. 18, 2014

(86) PCT No.: PCT/US2014/066197
§ 371 (c)(1),
(2) Date: May 17, 2016

(87) PCT Pub. No.: WO2015/074063
PCT Pub. Date: May 21, 2015

(65) Prior Publication Data
US 2016/0280766 A1 Sep. 29, 2016

Related U.S. Application Data

(60) Provisional application No. 61/905,549, filed on Nov. 18, 2013.

(51) Int. Cl.
| | |
|---|---|
| *C07K 16/00* | (2006.01) |
| *C12P 21/06* | (2006.01) |
| *C07K 16/28* | (2006.01) |
| *C07K 16/32* | (2006.01) |
| *C12P 21/02* | (2006.01) |
| *C07K 1/00* | (2006.01) |

(52) U.S. Cl.
CPC .......... *C07K 16/00* (2013.01); *C07K 16/2887* (2013.01); *C07K 16/32* (2013.01); *C12P 21/02* (2013.01); *C07K 2317/41* (2013.01); *C07K 2317/52* (2013.01); *C07K 2317/71* (2013.01); *C07K 2317/92* (2013.01)

(58) Field of Classification Search
None
See application file for complete search history.

(56) References Cited

U.S. PATENT DOCUMENTS

| 6,737,056 | B1 * | 5/2004 | Presta | C07K 16/4291 |
| | | | | 424/133.1 |
| 2006/0247425 | A1 | 11/2006 | Chung et al. | |
| 2009/0098124 | A1 | 4/2009 | Stavenhagen | |
| 2012/0010387 | A1 | 1/2012 | Niwa et al. | |
| 2012/0276092 | A1 * | 11/2012 | Luo | C07K 16/00 |
| | | | | 424/133.1 |
| 2015/0322135 | A1 * | 11/2015 | Ishino | C07K 16/00 |
| | | | | 424/133.1 |

FOREIGN PATENT DOCUMENTS

| WO | 2004/063351 | 7/2004 |
| WO | 2012/016073 | 2/2012 |
| WO | 2014/087299 | 6/2014 |

OTHER PUBLICATIONS

International Search Report dated Mar. 6, 2015 in corresponding International Application No. PCT/US2014/066197.
Abès et al., "Impact of Glycosylation on Effector Functions of Therapeutic IgG", Pharmaceuticals, vol. 3, pp. 146-157 (2010).
Sazinsky et al., "Aglycosylated immunoglobulin $G_1$ variants productively engage activating Fc receptors", PNAS, vol. 105, No. 51, pp. 20167-20172 (2008).
Extended European Search Report dated Jun. 14, 2017 in corresponding European Application No. 14862317.6.
Shakin-Eshleman et al., "The Amino Acid at the X Position of an Asn-X-Ser Sequon Is an Important Determinant of N-Linked Core-glycosylation Efficiency", The Journal of Biological Chemistry, 271(11):6363-6366 (1996).

* cited by examiner

*Primary Examiner* — Chun W Dahle
(74) *Attorney, Agent, or Firm* — Wenderoth, Lind & Ponack, L.L.P.

(57) ABSTRACT

Means for improving the effector functions of current immunotherapeutic antibodies through targeted hyper-glycosylation of the antibody Fc region are disclosed, as well as antibody variants having hyper-glycosylated Fc regions. Fc receptor-mediated effector functions have been shown to be a critical contributor to the efficacies of numerous therapeutic antibodies currently in clinical use. Targeted hyper-glycosylation of antibodies has the potential to significantly improve current immunotherapies for cancer.

16 Claims, 4 Drawing Sheets
Specification includes a Sequence Listing.

Figure 2

```
IgG2    ASTKGPSVFPLAPCSRSTSESTAALGCLVKDYFPEPVTVSWNSGALTSGVHTFPAVLQSS
IgG4    ASTKGPSVFPLAPCSRSTSESTAALGCLVKDYFPEPVTVSWNSGALTSGVHTFPAVLQSS
IgG1    ASTKGPSVFPLAPSSKSTSGGTAALGCLVKDYFPEPVTVSWNSGALTSGVHTFPAVLQSS
IgG3    ASTKGPSVFPLAPCSRSTSGGTAALGCLVKDYFPEPVTVSWNSGALTSGVHTFPAVLQSS
        *************.*:***  ***************************************

IgG2    GLYSLSSVVTVPSSNFGTQTYTCNVDHKPSNTKVDKTVER--------------------
IgG4    GLYSLSSVVTVPSSSLGTKTYTCNVDHKPSNTKVDKRVES--------------------
IgG1    GLYSLSSVVTVPSSSLGTQTYICNVNHKPSNTKVDKKVE---------------------
IgG3    GLYSLSSVVTVPSSSLGTQTYTCNVNHKPSNTKVDKRVELKTPLGDTTHTCPRCPEPKSC
        **************.:**:** ***:**********:**

226-228
IgG2    ------------------------------RCCVECPPCPAPPVAG-PSVFLFPPKPKDT
IgG4    ------------------------------KYGPPCPSCPAPEFLGGPSVFLFPPKPKDT
IgG1    ---------------------------PKSCDKTHTCPPCPAPELLGGPSVFLFPPKPKDT
IgG3    DTPPPCPRCPEPKSCDTPPPCPRCPEPKSCDTPPPCPRCPAPELLGGPSVFLFPPKPKDT
                                   ** ****  .  * . ************

290-292
IgG2    LMISRTPEVTCVVVDVSHEDPEVQFNWYVDGVEVHNAKTKPREEQFNSTFRVVSVLTVVH
IgG4    LMISRTPEVTCVVVDVSQEDPEVQFNWYVDGVEVHNAKTKPREEQFNSTYRVVSVLTVLH
IgG1    LMISRTPEVTCVVVDVSHEDPEVKFNWYVDGVEVHNAKTKPREEQYNSTYRVVSVLTVLH
IgG3    LMISRTPEVTCVVVDVSHEDPEVQFKWYVDGVEVHNAKTKPREEQYNSTFRVVSVLTVLH
        ****************:*****:*:*:***********************:***.****:*

IgG2    QDWLNGKEYKCKVSNKGLPAPIEKTISKTKGQPREPQVYTLPPSREEMTKNQVSLTCLVK
IgG4    QDWLNGKEYKCKVSNKGLPSSIEKTISKAKGQPREPQVYTLPPSQEEMTKNQVSLTCLVK
IgG1    QDWLNGKEYKCKVSNKALPAPIEKTISKAKGQPREPQVYTLPPSRDELTKNQVSLTCLVK
IgG3    QDWLNGKEYKCKVSNKALPAPIEKTISKTKGQPREPQVYTLPPSREEMTKNQVSLTCLVK
        ****************.**:.*******:***************::*.************

IgG2    GFYPSDISVEWESNGQPENNYKTTPPMLDSDGSFFLYSKLTVDKSRWQQGNVFSCSVMHE
IgG4    GFYPSDIAVEWESNGQPENNYKTTPPVLDSDGSFFLYSRLTVDKSRWQEGNVFSCSVMHE
IgG1    GFYPSDIAVEWESNGQPENNYKTTPPVLDSDGSFFLYSKLTVDKSRWQQGNVFSCSVMHE
IgG3    GFYPSDIAVEWESSGQPENNYNTTPPMLDSDGSFFLYSKLTVDKSRWQQGNIFSCSVMHE
        *******:*****.****************************************:*********

IgG2    ALHNHYTQKSLSLSPGK
IgG4    ALHNHYTQKSLSLSLGK
IgG1    ALHNHYTQKSLSLSPGK
IgG3    ALHNRFTQKSLSLSPGK
        ****::*********  **
```

HYPER-GLYCOSYLATED ANTIBODIES WITH SELECTIVE FC RECEPTOR BINDING

STATEMENT OF FEDERALLY SPONSORED RESEARCH AND DEVELOPMENT

This invention was made with government support under Grant No. AI090866 awarded by the National Institutes of Health. The government has certain rights in the invention.

TECHNICAL FIELD

The invention relates to the field of immunology, with particular reference to antibody variants having altered receptor binding affinities.

BACKGROUND OF INVENTION

Therapeutic antibodies are being used with increasing frequency and for expanding indications. For example, therapeutic antibodies are used to treat cancer by stimulating anti-tumor immune responses. In another example, therapeutic antibodies are used to treat autoimmune diseases by inhibiting immune responses to self-antigens.

Generally, antibody therapeutics are engineered to bind specifically to antigens (either foreign or self), often with modifications to their Fab regions that increase antibody affinity or avidity. Full-length antibodies include the Fc region that, when bound by Fc receptors on immune cells, triggers a range of effector functions (e.g., pro-inflammatory or anti-inflammatory responses), which contribute significantly to the mechanisms of action of such therapeutics.

The amino acid sequence of human antibody Fc regions is unchanged among all antibodies produced in the body within a given antibody subtype. Thus, while the Fab region provides variability for binding to different antigens, the Fc region provides a constant structure for recognition by Fc receptors.

A variety of human Fc receptor subtypes have been identified on cell surfaces, each binding antibodies through their Fc regions and triggering (or suppressing) particular immune responses depending on the identity of the cell expressing the Fc receptor and the subtype of the Fc receptor. The family of human Fc receptors includes both activating and inhibitory receptors that either induce or negatively modulate effector functions, respectively.

A substantial amount of research has been conducted with the aim of producing antibodies exhibiting selective binding to either activating or inhibitory Fc receptors. This work has revealed that IgG1 antibodies typically used as therapeutics contain a single glycan (carbohydrate moiety) per chain linked to the asparagine residue at position 297 (Asn297) (Radaev et al., (2001) *J. Biol. Chem.* 276:16478-16483). The presence of this glycan is critical for antibody binding to all Fc receptor subtypes and variations in its chemical composition can modulate Fc receptor binding affinities. Somewhat surprisingly, the majority of antibody/Fc receptor binding interfaces are composed of intermolecular contacts between amino acid residues from each of the two proteins, and do not involve atoms from the glycan linked to Asn297. Therefore, additional research has been conducted to determine whether modifications to the particular amino acids of antibodies found within this interface will result in the development of antibodies having predictable affinities for selected Fc receptor subtypes (Shields et al., (2001) *J. Biol. Chem.* 276:6591; Lazar et al., (2006) *Proc. Natl. Acad. Sci.* 103:4005-10; Richards et al., (2008) *Mol. Cancer Ther.* 7:2517-27; Chu et al., (2008) *Mol. Immunol.* 45:3926-33).

It can thus be seen that antibodies engineered to selectively bind either activating or inhibitory Fc receptors will likely exhibit improved therapeutic efficacy versus antibodies with wild-type Fc regions. For example, antibodies engineered to increase binding to activating Fc receptors and/or decrease binding to inhibitory Fc receptors could intensify effector functions that aid in the removal of malignant cells and, thus, function as improved versions of anti-cancer therapeutic antibodies. The present invention is directed to the development of such antibodies, as well as other important goals.

BRIEF SUMMARY OF INVENTION

The invention relates to improvements in the effector functions of current immunotherapeutic antibodies through targeted hyper-glycosylation of the antibody Fc region. Fc receptor-mediated effector functions have been shown to be a critical contributor to the efficacies of numerous therapeutic antibodies currently in clinical use. Targeted hyper-glycosylation of antibodies has the potential to significantly improve current immunotherapies for cancer.

In particular, the invention provides a series of hyper-glycosylated antibody variants that have been modified in the Fc region of the antibody to either enhance or reduce the affinity of the Fc region to the various Fc γ receptors (FcγRs) that are expressed on the surface of immune cells. FcγR interactions with immune complexes (i.e., antibodies bound specifically to antigens) trigger a wide range of pro-inflammatory or anti-inflammatory immune responses. Acquiring the ability to tightly regulate the immune response is important for the treatment of numerous diseases. In humans, activating receptors include FcγRIIA and FcγRIIIA, while the sole inhibitory receptor is FcγRIIB.

In a first embodiment, the invention is drawn to an antibody comprising a human IgG Fc region wherein the Fc region is hyper-glycosylated in comparison to a naturally-occurring version of the antibody. In certain aspects of this embodiment, the binding affinity of the antibody for an FcγR is decreased. In certain other aspects of this embodiment, the binding affinity of the antibody for an FcγR is increased.

In a second embodiment, the invention is drawn to an antibody comprising a human IgG Fc region wherein one or more triplets of three contiguous amino acids on one or both chains of the Fc region is replaced by an Asn-X-Thr/Ser triplet, wherein each X is any amino acid except proline, and wherein the Asn of the triplet is glycosylated, partially glycosylated or unglycosylated.

In certain aspects of this embodiment, the Fc region is altered to comprise one Asn-X-Thr/Ser triplet located in the same position on both chains of the Fc region. In certain aspects of this embodiment, the Fc region is altered to comprise two Asn-X-Thr/Ser triplets located in the same positions on both chains of the Fc region. In certain aspects of this embodiment, the Fc region is altered to comprise three Asn-X-Thr/Ser triplets located in the same positions on both chains of the Fc region.

In a third embodiment, the invention is drawn to an antibody comprising a human IgG Fc region wherein one or more triplets of three contiguous amino acids on one or both chains of the Fc region is replaced by an Asn-X-Thr/Ser triplet, wherein the triplets are independently located such that the Asn of the triplet is at one or more positions 217-235 and 287-292, wherein the positions correspond to the amino acid sequence of the human IgG1 heavy chain, wherein each X is any amino acid except proline, and wherein the Asn of the triplet is glycosylated, partially glycosylated or unglycosylated.

In certain aspects of this embodiment, the Fc region is altered to comprise one Asn-X-Thr/Ser triplet located in the same position on both chains of the Fc region. In certain aspects of this embodiment, the Fc region is altered to comprise two Asn-X-Thr/Ser triplets located in the same positions on both chains of the Fc region. In certain aspects of this embodiment, the Fc region is altered to comprise three Asn-X-Thr/Ser triplets located in the same positions on both chains of the Fc region.

In certain aspects of this embodiment, the Fc region is altered to comprise two Asn-X-Thr/Ser triplets located in the same positions on both chains of the Fc region, wherein one of the triplets is located such that the Asn of the triplet is at one of positions 217-235 and wherein the other triplet is located such that the Asn of the triplet is at one of positions 287-292. In exemplary aspects, one of the triplets is located such that the Asn of the triplet is at position 226 and the other triplet is located such that the Asn of the triplet is at position 290.

In a fourth embodiment, the invention is drawn to an antibody comprising a human IgG Fc region having amino acids corresponding to amino acids 226-228 of human IgG1 of one or both chains of the Fc region replaced by an Asn-X-Thr/Ser triplet, wherein each X is any amino acid except proline, and wherein Asn residues present at position 226 are glycosylated (Fc-226$^{hg}$, partially glycosylated or unglycosylated). In certain aspects, both chains of the Fc region have the noted Asn-X-Thr/Ser triplet at positions 226-228.

In a fifth embodiment, the invention is drawn to an antibody comprising a human IgG Fc region having amino acids corresponding to amino acids 290-292 of human IgG1 of one or both chains of the Fc region replaced by an Asn-X-Thr/Ser triplet, wherein each X is any amino acid except proline, and wherein Asn residues present at position 290 are glycosylated (Fc-290$^{hg}$), partially glycosylated or unglycosylated. In certain aspects, both chains of the Fc region have the noted Asn-X-Thr/Ser triplet at positions 290-292.

In a sixth embodiment, the invention is drawn to an antibody comprising a human IgG Fc region having amino acids corresponding to amino acids 226-228 of human IgG1 of one or both chains of the Fc region replaced by an Asn-X-Thr/Ser triplet and amino acids corresponding to amino acids 290-292 of human IgG1 of one or both chains of the Fc region replaced by an Asn-X-Thr/Ser triplet, wherein each X is any amino acid except proline, and wherein Asn residues present at positions 226 and 290 are glycosylated (Fc-226$^{hg}$/290$^{hg}$), partially glycosylated or unglycosylated. In certain aspects, both chains of the Fc region have the noted Asn-X-Thr/Ser triplet at positions 226-228 and 290-292.

In each of the first through sixth embodiments, the human IgG Fc region may be a human IgG1 Fc region, a human IgG2 Fc region, a human IgG3 Fc region or a human IgG4 Fc region.

In each of the first through sixth embodiments, the antibody may comprise one or more additional amino acid replacements selected from the group consisting of S298A, E333A, and K334A, corresponding to the amino acid sequence of human IgG1, each independently on one or both of the chains of the Fc region.

In each of the first through sixth embodiments, the antibody may comprise one or more additional amino acid replacements selected from the group consisting of S239D, I332E, and A330L, corresponding to the amino acid sequence of human IgG1, each independently on one or both of the chains of the Fc region.

In each of the first through sixth embodiments, the antibody may comprise a G236A amino acid replacement, corresponding to the amino acid sequence of human IgG1, on one or both of the chains of the Fc region.

In each of the first through sixth embodiments, the Asn-X-Thr/Ser triplets may be Asn-Ser-Thr.

In one aspect of each of the first through sixth embodiments, the Asn residues of the triplets are glycosylated.

In one non-limiting example of the invention, the antibody is an antibody comprising a human IgG Fc region having amino acids corresponding to amino acids 226-228 of human IgG1 of both chains of the Fc region replaced by Asn-Ser-Thr and amino acids corresponding to amino acids 290-292 of human IgG1 of both chains of the Fc region replaced by Asn-Ser-Thr, wherein Asn residues present at positions 226 and 290 are glycosylated, and wherein both heavy chains have a S298A amino acid replacement corresponding to the amino acid sequence of human IgG1 (Fc-226$^{hg}$/290$^{hg}$/S298A).

In a seventh embodiment, the present invention provides polynucleotides encoding the antibodies of the first through sixth embodiments.

In an eighth embodiment, the present invention provides vectors comprising one or more of the polynucleotides of the present invention.

In a ninth embodiment, the present invention provides host cells comprising one or more of the vectors of the present invention. In certain, non-limiting aspects, the cell lines are mammalian cell lines or yeast cell lines. As an example, the cell line is the HEK293 or CHO cell line.

In a tenth embodiment, the present invention provides a method of producing an antibody of the first through sixth embodiments, comprising culturing a host cell of the ninth embodiment in a culture media under conditions promoting production of the antibody and isolating the antibody from the culture media and a host cell. In certain aspects, the host cells are further cultured under conditions promoting glycosylation of Asn residues of the Asn-X-Thr/Ser triplets.

The present invention also comprises methods for altering the binding affinity of an antibody for an FcγR, wherein the antibody comprises a human IgG Fc region. Thus, and in an eleventh embodiment, the invention is drawn to a method for altering the binding affinity of an antibody for an FcγR comprising selecting an antibody having a human IgG Fc region, replacing one or more triplets of three contiguous amino acids on one or both chains of the Fc region by an Asn-X-Thr/Ser triplet, wherein each X is any amino acid except proline, and producing the antibody under conditions where the Asn residues of the triplets are glycosylated, partially glycosylated or unglycosylated.

In certain aspects of this embodiment, the Fc region is altered to comprise one Asn-X-Thr/Ser triplet located in the same position on both chains of the Fc region. In certain aspects of this embodiment, the Fc region is altered to comprise two Asn-X-Thr/Ser triplets located in the same positions on both chains of the Fc region. In certain aspects of this embodiment, the Fc region is altered to comprise three Asn-X-Thr/Ser triplets located in the same positions on both chains of the Fc region.

In a twelfth embodiment, the invention is drawn to a method for altering the binding affinity of an antibody for an FcγR comprising selecting an antibody having a human IgG Fc region, replacing one or more triplets of three contiguous amino acids on one or both chains of the Fc region by an Asn-X-Thr/Ser triplet, wherein the triplets are independently located such that the Asn of the triplet is at one or more of positions 217-235 and 287-292, wherein the positions correspond to the amino acid sequence of the human IgG1 heavy chain, wherein each X is any amino acid except proline, and producing the antibody under conditions where the Asn residues of the triplets are glycosylated, partially glycosylated or unglycosylated.

In certain aspects of this embodiment, the Fc region is altered to comprise one Asn-X-Thr/Ser triplet located in the same position on both chains of the Fc region. In certain aspects of this embodiment, the Fc region is altered to comprise two Asn-X-Thr/Ser triplets located in the same positions on both chains of the Fc region. In certain aspects of this embodiment, the Fc region is altered to comprise three Asn-X-Thr/Ser triplets located in the same positions on both chains of the Fc region.

In certain aspects of this embodiment, the Fc region is altered to comprise two Asn-X-Thr/Ser triplets located in the same positions on both chains of the Fc region, wherein one of the triplets is located such that the Asn of the triplet is at one of positions 217-235 and wherein the other triplet is located such that the Asn of the triplet is at one of positions 287-292, wherein the positions correspond to the amino acid sequence of the human IgG1 heavy chain. In exemplary aspects, one of the triplets is located such that the Asn of the triplet is at position 226 and the other triplet is located such that the Asn of the triplet is at position 290.

In a thirteenth embodiment, the invention is drawn to a method for altering the binding affinity of an antibody for an FcγR comprising selecting an antibody having a human IgG Fc region, replacing amino acids corresponding to amino acids 226-228 of human IgG1 of one or both chains of the Fc region with an Asn-X-Thr/Ser triplet wherein each X is any amino acid except proline, and producing the antibody under conditions where Asn residues present at position 226 are glycosylated, partially glycosylated or unglycosylated.

In a fourteenth embodiment the invention is drawn to a method for altering the binding affinity of an antibody for an FcγR comprising selecting an antibody having a human IgG Fc region, replacing amino acids corresponding to amino acids 290-292 of human IgG1 of one or both chains of the Fc region with an Asn-X-Thr/Ser triplet wherein each X is any amino acid except proline, and producing the antibody under conditions where Asn residues present at position 290 are glycosylated, partially glycosylated or unglycosylated.

In a fifteenth embodiment the invention is drawn to a method for altering the binding affinity of an antibody for an FcγR comprising selecting an antibody having a human IgG Fc region, replacing amino acids corresponding to amino acids 226-228 of human IgG1 of one or both chains of the Fc region with an Asn-X-Thr/Ser triplet, replacing amino acids corresponding to amino acids 290-292 of human IgG1 of one or both chains of the Fc region with an Asn-X-Thr/Ser triplet, wherein each X is any amino acid except proline, and producing the antibody under conditions where Asn residues present at positions 226 and 290 are glycosylated, partially glycosylated or unglycosylated.

In a sixteenth embodiment the invention is drawn to a method for altering the binding affinity of an antibody for an FcγR comprising selecting an antibody having a human IgG Fc region, replacing amino acids corresponding to amino acids 226-228 of human IgG1 of one or both chains of the Fc region with an Asn-X-Thr/Ser triplet, replacing amino acids corresponding to amino acids 290-292 of human IgG1 of one or both chains of the Fc region with an Asn-X-Thr/Ser triplet wherein each X is any amino acid except proline, making a S298A amino acid replacement in one or both of the heavy chains, wherein the location of the replacement corresponds to the amino acid sequence of human IgG1, and producing the antibody under conditions where Asn residues present at positions 226 and 290 are glycosylated, partially glycosylated or unglycosylated.

In each of the eleventh through sixteenth embodiments, the method may further comprise making one or more additional amino acid replacements selected from the group consisting of S298A, E333A, and K334A, each independently on one or both of the chains of the Fc region, wherein the location of the replacement corresponds to the amino acid sequence of human IgG1.

In each of the eleventh through sixteenth embodiments, the method may further comprise making one or more additional amino acid replacements selected from the group consisting of S239D, I332E, and A330L, each independently on one or both of the chains of the Fc region, wherein the location of the replacement corresponds to the amino acid sequence of human IgG1.

In each of the eleventh through sixteenth embodiments, the method may further comprise making a G236A amino acid replacement in one or both of the chains of the Fc region, wherein the location of the replacement corresponds to the amino acid sequence of human IgG1.

In each of the eleventh through sixteenth embodiments, the method may further comprise making a S298A amino acid replacement in one or both of the chains of the Fc region, wherein the location of the replacement corresponds to the amino acid sequence of human IgG1.

In each of the eleventh through sixteenth embodiments, the FcγR is selected from the group consisting of FcγRIIA, FcγRIIIA and FcγRIIB, and variants thereof that bind antibodies having an IgG Fc region or a functional fragment of such an Fc region.

In each of the eleventh through sixteenth embodiments, the binding affinity of the antibody for an FcγR is decreased.

In each of the eleventh through sixteenth embodiments, the binding affinity of the antibody for an FcγR is increased.

In each of the eleventh through sixteenth embodiments, the Asn-X-Thr/Ser triplets may be Asn-Ser-Thr.

In one aspect of each of the eleventh through sixteenth embodiments, the antibody is produced under conditions where the Asn residues of the triplets are glycosylated.

The foregoing has outlined rather broadly the features and technical advantages of the present invention in order that the detailed description of the invention that follows may be better understood. Additional features and advantages of the invention will be described herein, which form the subject of the claims of the invention. It should be appreciated by those skilled in the art that any conception and specific embodiment disclosed herein may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that any description, figure, example, etc. is provided for the purpose of illustration and description only and is by no means intended to define the limits the invention.

BRIEF DESCRIPTION OF DRAWINGS

FIG. 2 provides an amino acid sequence alignment of IgG subtype heavy chain sequences. Positions 226-228 and 290-292 are shown in boxes. IgG1=SEQ ID NO:8; IgG2=SEQ ID NO:9; IgG3=SEQ ID NO: 10; IgG4=SEQ ID NO:11.

DETAILED DESCRIPTION OF THE INVENTION

I. Definitions

Figure 1:
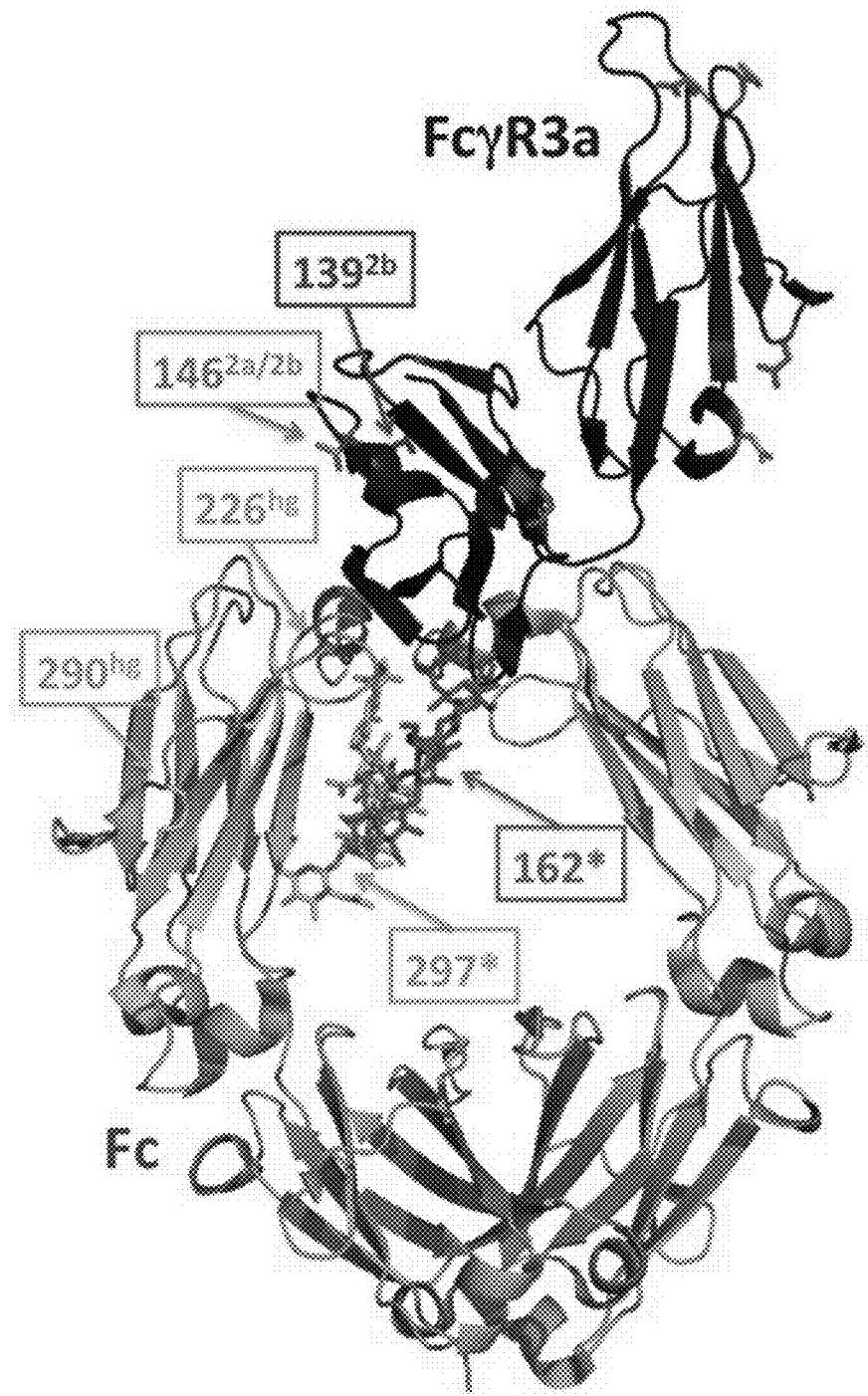
FIG. 1 shows the structure of the Fc/FcγRIIIA complex. The glycan attached to Fc Asn297 is indicated by an arrow, as are additional engineered glycan sites ("hg") at amino acid positions 226 and 290. The FcγRIIIA glycan site at amino acid position 162 is indicated by an arrow, as are the FcγRIIA/IIB sites at amino acid position 146, and the unique FcγRIIB site at amino acid position 139.

Unless otherwise noted, technical terms are used according to conventional usage. Definitions of common terms in molecular biology may be found, for example, in Benjamin Lewin, Genes VII, published by Oxford University Press, 2000 (ISBN 019879276X); Kendrew et al. (eds.); The Encyclopedia of Molecular Biology, published by Blackwell Publishers, 1994 (ISBN 0632021829); and Robert A. Meyers (ed.), Molecular Biology and Biotechnology: a Comprehensive Desk Reference, published by Wiley, John & Sons, Inc., 1995 (ISBN 0471186341); and other similar technical references.

As used herein, "a" or "an" may mean one or more. As used herein when used in conjunction with the word "comprising," the words "a" or "an" may mean one or more than one. As used herein "another" may mean at least a second or more. Furthermore, unless otherwise required by context, singular terms include pluralities and plural terms include the singular.

As used herein, "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

II. The Present Invention

Monoclonal IgG antibodies have become an increasingly important class of therapeutic agents for cancer treatment (Reichert et al., (2007) Nat Rev Drug Discov 6:349-356). These antibodies can specifically recognize target cancer cells via their Fab regions and recruit effector cells from the immune system through Fc region engagement of Fcγ receptors (FcγRs). Most immunotherapeutic antibodies require both mechanisms, i.e., Fab-mediated antigen binding and Fc-mediated effector function induction, for maximal efficacy. Antibodies used for tumor immunotherapy might then be improved by engineering the Fc region with optimal affinities for certain FcγRs to increase effector function activation and the killing of antibody-coated tumor cells.

Receptors in the FcγR family can be categorized according to the type of signaling pathway that each triggers—that is, whether they are inhibitory or activating (Nimmerjahn et al., (2008) Nat Rev Immunol 8:34-47). Engagement of activating FcγRs (e.g., FcγRIIA and FcγRIIIA) induces various effector functions (Nimmerjahn et al., (2008) Nat Rev Immunol 8:34-47), including antibody-dependent cellular cytotoxicity (ADCC), while binding to the sole inhibitory receptor, FcγRIIB, represses these functions. Emerging clinical data demonstrate a correlation between the clinical response to some therapeutic antibodies and expression of high affinity activating FcγR alleles (Cartron et al., (2002) Blood 99:754-758; Musolino et al., (2008) J Clin Oncol 26:1789-1796; Weng et al., (2009) Leuk Lymphoma 50:1494-1500). Furthermore, studies using knockout mice showed that elimination of the inhibitory receptor resulted in significantly increased potency of anti-tumor mAbs (Clynes et al., (2000) Nat Med 6:443-446; Green et al. (2002) Cancer Res 62:6891-6900 (2002); Nimmerjahn et al (2005), Science 310: 1510-1512). These data indicate that antibodies engineered with increased affinity to activating FcγRs and/or reduced affinity to the inhibitory FcγR could have significantly enhanced in vivo anti-tumor activities (Nimmerjahn et al (2005), Science 310: 1510-1512).

Difficulties have been encountered in engineering human IgG antibody Fc variants to bind selectively to activating versus inhibitory FcγRs, largely due to three aspects of the Fc-FcγR interaction: (1) there is a glycan moiety attached to Asn297 of the Fc region which lies within the binding site for all FcγRs and is required for all FcγR binding; (2) each FcγR adopts a nearly identical position when in complex with an antibody Fc domain; and (3) FcγRs have high sequence similarity. Thus, it will be apparent that changes in carbohydrate structure and amino acid sequence can affect Fc binding to each of the FcγRs, i.e., most Fc mutations affect binding to all FcγRs similarly.

Described herein is a new generation of antibody immunotherapeutics that overcome the problems encountered in the past. Targeted hyper-glycosylation of the Fc region of IgG antibodies currently used in the clinic results in improved antibody profiles. Glycans are uniquely positioned on each FcγR, providing unique macromolecular surfaces to target for differential binding. Each FcγR has a distinct number of natural N-linked glycosylation sites—FcγRIIA has two, FcγRIIB has three and FcγRIIIA has five. Of these, only the glycan at position Asn162 of FcγRIIIA is involved in Fc binding. However, some of the remaining glycans in the FcγR proteins reside near the Fc-FcγR interface (FIG. 1).

The present inventors hypothesized that by engineering human IgG Fc regions bearing additional glycans beyond that attached to Asn297, hyper-glycosylated antibody variants could be generated where the added bulky carbohydrate group (with molecular volumes equivalent to ~⅓ that of a single Ig domain) could make contacts with the glycans that are distinct to each FcγR, thereby altering binding affinities selectively to each FcγR.

The technology described herein thus comprises incorporating additional glycosylation moieties at distinct sites in the Fc region of antibodies to specifically expand the Fc-FcγR binding interface, such that the carbohydrates located at different positions on various FcγRs can significantly affect binding affinity and specificity. It has been found that antibodies modified by targeted hyper-glycosylation technology described herein exhibit significantly reduced binding to inhibitory versus activating FcγRs.

As described in more detail below, eleven hyper-glycosylated IgG1 Fc variants were produced in which a single additional N-linked glycosylation site was generated outside, but near, the Fc-FcγR binding interface, predominantly in the apical loops of the Cγ3 domain facing the FcγR. However, two of these hyper-glycosylated variants, Fc-226$^{hg}$ (having one additional glycan on an asparagine engineered at position 226, i.e., hyper-glycosylated at position 226 of the heavy chain) and Fc-290$^{hg}$ (having one additional glycan on an asparagine engineered at position 290 of the heavy chain), exhibit decreased binding to FcγRIIB with smaller changes in binding to FcγRIIIA and to FcγRIIA. FcγR binding was also tested on Fc-$226^{hg}$/$290^{hg}$, a doubly hyper-glycosylated variant having glycans on asparagines engineered at positions 226 and 290 of the heavy chain. FcγR binding was further tested on variants of Fc-$226^{hg}$/$290^{hg}$ where additional amino acid changes were made based on published information regarding changes that increased binding to activating FcγRs (Shields et al., (2001) J. Biol. Chem. 276:6591-6604). One such variant, Fc-$226^{hg}$/$290^{hg}$/S298A, exhibited at least 60-fold reduced binding to the inhibitory FcγRIIB relative to wild type IgG1 Fc, with only 6-fold and 10-fold reduced binding to the activating receptors FcγRIIIA and FcγRIIA, respectively. Such an engineered antibody might de-repress FcγR-mediated effector functions in vivo resulting in more effective therapeutic antibodies for treating cancer.

Antibodies

The present invention thus provides IgG antibody variants with hyper-glycosylation within the Fc region of the antibody. In these antibody variants, the additional glycosylation is positioned on asparagine residues within the Fc region of the antibody. Because the IgG Fc region only contains one asparagine thought to play a role in Fc-FcγR binding (at position 297), the antibody variants of the invention are modified to include one or more additional asparagine residues in the Fc region of the antibodies, and the invention includes such antibody variants wherein the one or more additional asparagine residues have not yet been glycosylated. Suitable positions for the additional asparagines include one or more of positions 217-235 and 287-292, corresponding to the IgG1 heavy chain amino acid sequence, numbered from the amino terminus of the polypeptide sequence (see FIG. 2). Exemplary positions include 226 and 290.

The IgG antibodies can be modified to include the additional asparagine residues through a number of different means well known to the skilled artisan. For example, cDNA encoding the IgG heavy chain of a selected antibody can be synthesized and cloned into a mammalian expression plasmid (e.g., pcDNA3.3 from Life Technologies). Mutations can then be made to the cDNA sequence using site-directed mutagenesis, for example. Other suitable means for producing the antibody variants include synthesizing the gene de novo, inclusive of the hyper-glycosylation mutations.

Once polynucleotides encoding the antibody variants are produced, they can be expressed in cell lines that include the means to produce and express the antibodies. Such cell lines may also include the means to glycosylate the asparagine residues, whether partially or fully. For example, polynucleotides encoding light and heavy chain sequences can be expressed in cell lines such as human embryonic kidney 293 (HEK293) or Chinese Hamster Ovary (CHO) cells. Glycosylation of asparagine occurs naturally in such cell lines during protein maturation through the Golgi and endoplasmic reticulum.

Asparagine is typically glycosylated through the addition of branched carbohydrates to N-acetylglucosamine.

Means are known and available for confirming proper glycosylation of the antibody variants. Such means include analyses by polyacrylamide gel electrophoresis (SDS-PAGE), lectin arrays and mass spectrometry.

In addition to modification of the antibody variants of the present invention through the addition of glycosylated asparagines, the antibody variants may also be modified to include selected amino acids in the Fc region that have previously been shown to play a role in Fc-FcγR interactions. For example, the antibody variants of the invention can also contain one, two or all three of the following IgG heavy chain mutations: S298A, E333A, K334A. The triple mutant S298A/E333A/K334A has been shown to significantly improve antibody-dependent cell-mediated cytotoxicity (ADCC) due to increased binding of the activating receptor FcγRIIIA (see, e.g., Shields et al., (2001) *J. Biol. Chem.* 276:6591). Moreover, the antibody variants of the invention can also contain one, two or all three of the following IgG heavy chain mutations: S239D, I332E, A330L. The double (S239D/I332E) and triple mutants have been shown to display more than two orders of magnitude enhancement of in vitro effector function (these mutants had a higher affinity for FcγRIIIA but also increased binding to FcγRIIA and FcγRIIB (see, e.g., Lazar et al., (2006) *Proc. Natl. Acad. Sci.* 103:4005-10). The antibody variants of the invention can also include the mutation G236A, which has been shown to exhibit a higher affinity for the receptor FcγRIIA while maintaining the same binding to FcγRIIIA and FcγRIIB (see, e.g., Richards et al., (2008) *Mol. Cancer Ther.* 7:2517-27).

The antibody variants of the invention will generally have the same amino acid modification on both heavy chains of the antibody. However, the invention expressly includes antibody variants where only one of the heavy chains contains a selected amino acid change. For example, the invention includes antibody variants where only one of the heavy chains is modified to include a asparagine at position 226 that may undergo glycosylation. It should be understood that in some cases, the antibody will include both instances of a first change (e.g., asparagine at position 226 on both heavy chains) but only one of a second change (e.g., S298A on only one of the heavy chains). Nothing in this disclosure should be viewed as a limitation on the potential combination of changes that may be made to the antibody variants of the invention.

As the antibody variants may prove useful even when they do not activate an FcγR (e.g., where they occupy the receptor and block binding by another molecule), the invention also includes antibody variants that lack the ability to activate or inhibit an FcγR upon binding. However, each of the antibody variants of the invention can be defined as having the ability to be bound by one or more FcγRs.

As will be clear to the skilled artisan, any IgG antibody has the potential to be altered to include one or more of the Fc region modifications described herein. When therapeutic antibodies are prepared that include one or more of the modifications, binding affinities for select Fc receptors can be changed in a desired manner, and the modified therapeutic antibodies may prove to have enhanced therapeutic activities. Examples of specific therapeutic antibodies that might be altered to include one or more of the Fc region modifications described herein include (i) antibodies having therapeutic activity, such as Avastin, Herceptin (Trastuzumab) and Rituxan (Rituximab), (ii) antibodies conjugated to drugs or other therapeutic agents. The antibody variants disclosed herein can be used as a platform technology and applied to improving existing immunotherapies as well as enhancing new monoclonal antibody biologics to be developed.

In addition to Avastin, Herceptin (Trastuzumab) and Rituxan (Rituximab), other antibodies having therapeutic activity encompassed within the scope of the invention include, but are not limited to, 3F8, 8H9, Abagovomab, Abciximab, Actoxumab, Adalimumab, Adecatumumab, Aducanumab, Afelimomab, Afutuzumab, Alacizumab pegol, ALD518, Alemtuzumab, Alirocumab, Altumomab pentetate, Amatuximab, Anatumomab mafenatox, Anifrolumab, Anrukinzumab, Apolizumab, Arcitumomab, Aselizumab, Atinumab, Atlizumab, Atorolimumab, Bapineuzumab, Basiliximab, Bavituximab, Bectumomab, Belimumab, Benralizumab, Bertilimumab, Besilesomab, Bevacizumab, Bezlotoxumab, Biciromab, Bimagrumab, Bivatuzumab mertansine, Blinatumomab, Blosozumab, Brentuximab vedotin, Briakinumab, Brodalumab, Canakinumab, Cantuzumab mertansine, Cantuzumab ravtansine, Caplacizumab, Capromab pendetide, Carlumab, Catumaxomab, cBR96-doxorubicin immunoconjugate, CC49, Cedelizumab, Certolizumab pegol, Cetuximab, Ch.14.18, Citatuzumab bogatox, Cixutumumab, Clazakizumab, Clenoliximab, Clivatuzumab tetraxetan, Conatumumab, Concizumab, CR6261, Crenezumab, Dacetuzumab, Daclizumab, Dalotuzumab, Daratumumab, Demcizumab, Denosumab, Detumomab, Dorlimomab aritox, Drozitumab, Duligotumab, Dupilumab, Dusigitumab, Ecromeximab, Eculizumab, Edobacomab, Edrecolomab, Efalizumab, Efungumab, Eldelumab, Elotuzumab, Elsilimomab, Enavatuzumab, Enlimomab pegol, Enokizumab, Enoticumab, Ensituximab, Epitumomab cituxetan, Epratuzumab, Erlizumab, Ertumaxomab, Etaracizumab, Etrolizumab, Evolocumab, Exbivirumab, Fanolesomab, Faralimomab, Farletuzumab, Fasinumab, FBTA05, Felvizumab, Fezakinumab, Ficlatuzumab, Figitumumab, Flanvotumab, Fontolizumab, Foralumab, Foravirumab, Fresolimumab, Fulranumab, Futuximab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Igovomab, IMAB362, Imciromab, Imgatuzumab, Inclacumab, Indatuximab ravtansine, Infliximab, Inolimomab, Inotuzumab ozogamicin, Intetumumab, Ipilimumab, Iratumumab, Itolizumab, Ixekizumab, Keliximab, Labetuzumab, Lambrolizumab, Lampalizumab, Lebrikizumab, Lemalesomab, Lerdelimumab, Lexatumumab, Libivirumab, Ligelizumab, Lintuzumab, Lirilumab, Lodelcizumab, Lorvotuzumab mertansine, Lucatumumab, Lumiliximab, Mapatumumab, Margetuximab, Maslimomab, Matuzumab, Mavrilimumab, Mepolizumab, Metelimumab, Milatuzumab, Minretumomab, Mitumomab, Mogamulizumab, Morolimumab, Motavizumab, Moxetumomab pasudotox, Muromonab-CD3, Nacolomab tafenatox, Namilumab, Naptumomab estafenatox, Narnatumab, Natalizumab, Nebacumab, Necitumumab, Nerelimomab, Nesvacumab, Nimotuzumab, Nivolumab, Nofetumomab merpentan, Ocaratuzumab, Ocrelizumab, Odulimomab, Ofatumumab, Olaratumab, Olokizumab, Omalizumab, Onartuzumab, Ontuxizumab, Oportuzumab monatox, Oregovomab, Orticumab, Otelixizumab, Otlertuzumab, Oxelumab, Ozanezumab, Ozoralizumab, Pagibaximab, Palivizumab, Panitumumab, Pankomab, Panobacumab, Parsatuzumab, Pascolizumab, Pateclizumab, Patritumab, Pemtumomab, Perakizumab, Pertuzumab, Pexelizumab, Pidilizumab, Pinatuzumab vedotin, Pintumomab, Placulumab, Polatuzumab vedotin, Ponezumab, Priliximab, Pritoxaximab, Pritumumab, PRO 140, Quilizumab, Racotumomab, Radretumab, Rafivirumab, Ramucirumab, Ranibizumab, Raxibacumab, Regavirumab, Reslizumab, Rilotumumab, Rituximab, Robatumumab, Roledumab, Romosozumab, Rontalizumab, Rovelizumab, Ruplizumab, Samalizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tanezumab, Taplitumomab paptox, Tefibazumab, Telimomab aritox, Tenatumomab, Teneliximab, Teplizumab, Teprotumumab, TGN1412, Ticilimumab, Tigatuzumab, Tildrakizumab, TNX-650, Tocilizumab, Toralizumab, Tositumomab, Tovetumab, Tralokinumab, Trastuzumab, TRBS07, Tregalizumab, Tremelimumab, Tucotuzumab celmoleukin, Tuvirumab, Ublituximab, Urelumab, Urtoxazumab, Ustekinumab, Vantictumab, Vapaliximab, Vatelizumab, Vedolizumab, Veltuzumab, Vepalimomab, Vesencumab, Visilizumab, Volociximab, Vorsetuzumab mafodotin, Votumumab, Zalutumumab, Zanolimumab, Zatuximab, Ziralimumab, and Zolimomab aritox.

The antibody variants of the invention need not be completely "human" antibodies or based on completely "human" antibodies. While the antibody variants of the invention need to possess an Fc region that will be recognized by human FcγRs, the antibody variants can be fully human antibodies in sequence, humanized antibodies, antibodies built on human heavy chain frameworks, or murine/human chimeric antibodies (e.g., consisting of murine Fab regions and human Fc regions).

It should be understood that the antibody variants of the invention are not limited to complete antibodies, but also includes various antibody fragments and modified versions of the antibody variants. The only limitation is that the antibody fragments modified versions include at least a portion of the Fc region such that the antibody variant can be bound by an FcγR. As the antibody variants may prove useful even when they do not activate an FcγR (e.g., where they occupy the receptor and block binding by another molecule), the antibody fragments described herein need not activate or inhibit an FcγR upon binding. Suitable fragments and modified versions include ScFv-Fc, minibodies, heavy chain antibodies, and trifunctional antibodies.

Antibody variants of the invention include the following groups.

The invention includes antibodies that comprise a human IgG Fc region wherein the Fc region is hyper-glycosylated in comparison to a naturally-occurring version of the antibody. As discussed above, the hyper-glycosylation stems from the alteration of one or both chains of the Fc region to include additional asparagine resides. The additional residues are glycosylated and, as a result, the antibody as a whole is hyper-glycosylated in comparison to the same antibody that was not altered to include additional asparagine residues (i.e., the naturally-occurring version of the antibody). In certain aspects of this embodiment, the binding affinity of the antibody for an FcγR is decreased. In certain other aspects of this embodiment, the binding affinity of the antibody for an FcγR is increased.

The invention includes antibodies that comprise a human IgG Fc region wherein one or more triplets of three contiguous amino acids on one or both chains of the Fc region is replaced by an Asn-X-Thr/Ser triplet, wherein each X is any amino acid except proline, and wherein the Asn of the triplet is glycosylated, partially glycosylated or unglycosylated. The Asn-X-Thr/Ser triplet is the consensus sequence for N-linked glycosylation. It should be understood that each reference to 'three contiguous amino acids on one or both chains of the Fc region' or an equivalent phrase means that one, two or three of the amino acids in the trio is changed so that the trio is encompassed by the definition of the Asn-X-Thr/Ser triplet. For example, if the third amino acid in the selected trio is Thr or Ser, then it will not be changed when the trio is altered to be encompassed by the Asn-X-Thr/Ser triplet.

In certain aspects, the Fc region of these antibodies is altered to comprise one Asn-X-Thr/Ser triplet located in the same position on both chains of the Fc region (e.g., the Fc region is altered to have Asn-Thr-Ser at positions 226-228 on both chains). In certain aspects, the Fc region of these antibodies is altered to comprise two Asn-X-Thr/Ser triplets located in the same positions on both chains of the Fc region. In certain aspects, the Fc region of these antibodies is altered to comprise three Asn-X-Thr/Ser triplets located in the same positions on both chains of the Fc region.

The invention includes antibodies that comprise a human IgG Fc region wherein one or more triplets of three contiguous amino acids on one or both chains of the Fc region is replaced by an Asn-X-Thr/Ser triplet, wherein the triplets are independently located such that the Asn of the triplet is at one or more of positions 217-235 and 287-292, wherein the positions correspond to the amino acid sequence of the human IgG1 heavy chain, wherein each X is any amino acid except proline, and wherein the Asn of the triplet is glycosylated, partially glycosylated or unglycosylated.

In certain aspects, the Fc region of these antibodies is altered to comprise one Asn-X-Thr/Ser triplet located in the same position on both chains of the Fc region. In certain aspects of this embodiment, the Fc region is altered to comprise two Asn-X-Thr/Ser triplets located in the same positions on both chains of the Fc region. In certain aspects of this embodiment, the Fc region is altered to comprise three Asn-X-Thr/Ser triplets located in the same positions on both chains of the Fc region.

In certain aspects, the Fc region of these antibodies is altered to comprise two Asn-X-Thr/Ser triplets located in the same positions on both chains of the Fc region, wherein one of the triplets is located such that the Asn of the triplet is at one of positions 217-235 and wherein the other triplet is located such that the Asn of the triplet is at one of positions 287-292. In exemplary aspects, one of the triplets is located such that the Asn of the triplet is at position 226 and the other triplet is located such that the Asn of the triplet is at position 290.

The invention includes antibodies that comprise a human IgG Fc region having amino acids corresponding to amino acids 226-228 of human IgG1 of one or both chains of the Fc region replaced by an Asn-X-Thr/Ser triplet, wherein each X is any amino acid except proline, and wherein Asn residues present at position 226 are glycosylated, partially glycosylated or unglycosylated. In certain aspects, both chains of the Fc region have the noted Asn-X-Thr/Ser triplet at positions 226-228.

The invention includes antibodies that comprise a human IgG Fc region having amino acids corresponding to amino acids 290-292 of human IgG1 of one or both chains of the Fc region replaced by an Asn-X-Thr/Ser triplet, wherein each X is any amino acid except proline, and wherein Asn residues present at position 290 are glycosylated, partially glycosylated or unglycosylated. In certain aspects, both chains of the Fc region have the noted Asn-X-Thr/Ser triplet at positions 290-292.

The invention includes antibodies that comprise a human IgG Fc region having amino acids corresponding to amino acids 226-228 of human IgG1 of one or both chains of the Fc region replaced by an Asn-X-Thr/Ser triplet and amino acids corresponding to amino acids 290-292 of human IgG1 of one or both chains of the Fc region replaced by an Asn-X-Thr/Ser triplet, wherein each X is any amino acid except proline, and wherein Asn residues present at positions 226 and 290 are glycosylated, partially glycosylated or unglycosylated. In certain aspects, both chains of the Fc region have the noted Asn-X-Thr/Ser triplet at positions 226-228 and 290-292.

Specific examples of the antibody variants of the invention include the following.

Fc-226$^{hg}$—the Fc-226$^{hg}$ antibody variant is an antibody comprising a human IgG Fc region. The IgG Fc region has amino acids corresponding to amino acids 226-228 of human IgG1 of one or both chains of the Fc region replaced by Asn-Ser-Thr, and Asn residues present at position 226 are glycosylated, partially glycosylated or unglycosylated. By replacing the amino acids that naturally occur at positions corresponding to amino acids 226-228 of human IgG1 with Asn-Ser-Thr, at least one additional site for N-linked glycosylation is provided in the Fc region of the antibody. While asparagine serves as the site of glycosylation, Ser-Thr are included as the triplet Asn-Ser-Thr is the full consensus sequence for N-linked glycosylation. In a specific aspect, the amino acids corresponding to amino acids 226-228 of both chains are replaced by Asn-Ser-Thr.

Fc-290$^{hg}$—the Fc-290$^{hg}$ antibody variant is an antibody comprising a human IgG Fc region. The IgG Fc region has amino acids corresponding to amino acids 290-292 of human IgG1 of one or both chains of the Fc region replaced by Asn-Ser-Thr, and Asn residues present at position 290 are glycosylated, partially glycosylated or unglycosylated. By replacing the amino acids that naturally occur at positions corresponding to amino acids 290-292 of human IgG1 with Asn-Ser-Thr, at least one additional site for N-linked glycosylation is provided in the Fc region of the antibody. In a specific aspect, the amino acids corresponding to amino acids 290-292 of both chains are replaced by Asn-Ser-Thr.

Fc-226$^{hg}$/290$^{hg}$—the Fc-290$^{hg}$/290$^{hg}$ antibody variant is an antibody comprising a human IgG Fc region. The IgG Fc region has amino acids corresponding to amino acids 226-228 of human IgG1 of one or both chains of the Fc region replaced by Asn-Ser-Thr and amino acids corresponding to amino acids 290-292 of human IgG1 of one or both chains of the Fc region replaced by Asn-Ser-Thr. Further, Asn residues present at positions 226 and 290 are glycosylated, partially glycosylated or unglycosylated. By replacing the amino acids that naturally occur at positions corresponding to amino acids 226-228 and 290-292 of human IgG1 with Asn-Ser-Thr, at least two additional sites for N-linked glycosylation are provided in the Fc region of the antibody. In a specific aspect, the amino acids corresponding to amino acids 226-228 and 292-292 of both chains are replaced by Asn-Ser-Thr.

Fc-226$^{hg}$/S298A—the Fc-226$^{hg}$/S298A antibody variant is an antibody comprising a human IgG Fc region. The IgG Fc region has amino acids corresponding to amino acids 226-228 of human IgG1 of one or both chains of the Fc region replaced by Asn-Ser-Thr, Asn residues present at position 226 are glycosylated, partially glycosylated or unglycosylated, and one or both heavy chains have a S298A amino acid replacement wherein the location of the replacement corresponds to the amino acid sequence of human IgG1. In a specific aspect, the amino acids corresponding to amino acids 226-228 of both chains are replaced by Asn-Ser-Thr.

Fc-290$^{hg}$/S298A—the Fc-290$^{hg}$/S298A antibody variant is an antibody comprising a human IgG Fc region. The IgG Fc region has amino acids corresponding to amino acids 290-292 of human IgG1 of one or both chains of the Fc region replaced by Asn-Ser-Thr, Asn residues present at position 290 are glycosylated, partially glycosylated or unglycosylated, and one or both heavy chains have a S298A amino acid replacement wherein the location of the replacement corresponds to the amino acid sequence of human IgG1. In a specific aspect, the amino acids corresponding to amino acids 290-292 of both chains are replaced by Asn-Ser-Thr.

Fc-226$^{hg}$/290$^{hg}$/S298A—the Fc-290$^{hg}$/290$^{hg}$/S298A antibody variant is an antibody comprising a human IgG Fc region. The IgG Fc region has amino acids corresponding to amino acids 226-228 of human IgG1 of one or both chains of the Fc region replaced by an Asn-X-Thr/Ser triplet and amino acids corresponding to amino acids 290-292 of human IgG1 of one or both chains of the Fc region replaced by Asn-Ser-Thr. Further, Asn residues present at positions 226 and 290 are glycosylated, partially glycosylated or unglycosylated and one or both heavy chains have a S298A amino acid replacement wherein the location of the replacement corresponds to the amino acid sequence of human IgG1. In a specific aspect, the amino acids corresponding to amino acids 226-228 and 290-292 of both chains are replaced by Asn-Ser-Thr.

In each of these specific examples of the antibody variants of the invention, the human IgG Fc region may be a human IgG1 Fc region, a human IgG2 Fc region, a human IgG3 Fc region or a human IgG4 Fc region. As shown by the amino acid sequence alignment in FIG. 2, there is a very high degree of homology between the IgG subtypes and the modifications described herein should have a comparable effect regardless of the IgG subtype of the antibody variant.

In each of these specific examples of the antibody variants of the invention, the antibody may comprise one or more additional amino acid replacements selected from the group consisting of G236A, 5239D, 5298A, A330L, I332E, E333A, and K334A, corresponding to the amino acid sequence of human IgG1, each independently on one or both of the chains of the Fc region. Thus, the antibody variants of the invention may include one, two, three, four, five, six or all seven of these amino acid replacements, in any combination, wherein the replacements are individually present on one or both of the heavy chains. In particular examples, the antibodies may comprise one or more additional amino acid replacements selected from the group consisting of S298A, E333A, and K334A; one or more additional amino acid replacements selected from the group consisting of S239D, I332E, and A330L; or a G236A amino acid replacement.

In each of the antibody variants of the invention, the Asn-X-Thr/Ser triplets may be Asn-Ser-Thr.

In each of these specific examples of the antibody variants of the invention, the glycosylation on Asn may be any of the typical glycan structures found on Asn residues in human antibodies (asparagine is typically glycosylated through the addition of branched carbohydrates to N-acetylglucosamine), for example, the glycan may be composed of N-acetyl galactosamine, galactose, neuraminic acid, N-acetylglucosamine, fructose, mannose, fucose, or other monosaccharides. Specific glycan structures include those provided in Kaneko, Y F, et al. 2006 Science 313:670-673.

It should be clear from the description of the invention that all references to the antibodies of the invention, e.g., the antibody variants, the antibody fragments, and the modified versions of the antibody variants, includes antibodies where the Asn residues of the Asn-X-Thr/Ser triplets are individually fully glycosylated, partially glycosylated or unglycosylated. For example, the antibody variants may be produced in a cell line that is unable to glycosylate the Asn residues. Such antibody variants could then undergo further manipulations to achieve the desired Asn glycosylation.

The antibody variants of the invention can be generated and tested as described in the Examples below.

Polynucleotides

The invention further encompasses polynucleotide molecules that encode the antibody variants, antibody fragments and modified versions of the antibody variants, as defined herein. The polynucleotide molecules include genomic DNA that has been mutated to include the noted Asn-X-Thr/Ser triplets, as well as cDNA that encodes the antibodies of the invention. As used herein "polynucleotides" may include polynucleotides that encode only the antibody heavy chain, i.e., that encode the Fc region, encode only the light chain, or encode both the heavy chain and the light chain on the same molecule. Thus, when reference is made to the use of polynucleotides encoding an antibody variant, for example, the polynucleotides may be genomic DNA or cDNA that encodes the heavy chain alone, the light chain alone, or both the heavy and light chain. The skilled artisan will understand that reference herein to the "heavy chain" means that portion of the antibody that includes the Fc region. Where an antibody fragment or modified version of an antibody variant does not include the complete heavy chain, reference herein to the polynucleotides encoding the heavy chain will be understood to mean the polynucleotides encoding at least the Fc region or functional fragment thereof.

Vectors and Cell Lines

Moreover, the invention encompasses vectors, such as plasmid expression vectors, that comprise one or more of the polynucleotides encoding the antibodies as defined herein. The vector into which the polynucleotide is inserted may any one of a variety of vectors for expressing a polypeptide. Such vectors include chromosomal, non-chromosomal and synthetic DNA sequences, e.g., derivatives of SV40, bacterial plasmids, phage DNA, yeast plasmids, vectors derived from combinations of plasmids and phage DNA, viral DNA such as vaccinia, adenovirus, fowl pox virus, and pseudorabies. Any other plasmid or vector may be used so long as it is replicable and viable in the host cell. The vector containing the polynucleotide may contain an appropriate promoter or control sequence. The vector may contain at least one selectable marker gene to provide a phenotypic trait for selection of transformed host cells. Such markers include, but are not limited to, dihydrofolate reductase (DHFR) or neomycin resistance for eukaryotic cell culture, and tetracycline or ampicillin resistance for culturing in E. coli and other bacteria. As an example, the pcDNA 3.1 vector is a suitable vector.

The invention also encompasses a host cell comprising one or more of the vectors of the present invention. In certain, non-limiting aspects, the host cell includes, but is not limited to: bacterial cells, such as *E. coli, Salmonella typhimurium*, fungal cells, such as yeast, insect cells, such as *Drosophila* S2 and *Spodoptera* Sf19, and animal cells such as CHO, COS, and Bowes melanoma. In particular examples, the host cell is a mammalian cell line or a yeast cell line, such as the HEK293 or CHO cell line.

The invention further provides a method for producing the antibody variants, antibody fragments and modified versions of the antibody variants, as defined herein, comprising culturing a host cell of the invention in a culture media under conditions promoting production of the antibody and isolating the antibody from the culture media and a host cell.

Methods

The invention also encompasses methods for altering the binding affinity of an antibody for an FcγR, wherein the antibody comprises a human IgG Fc region.

In a first embodiment of the method, the invention is drawn to a method for altering the binding affinity of an antibody for an FcγR comprising selecting an antibody having a human IgG Fc region, replacing one or more triplets of three contiguous amino acids on one or both chains of the Fc region by an Asn-X-Thr/Ser triplet, wherein each X is any amino acid except proline, and producing the antibody under conditions where the Asn residues of the triplets are glycosylated.

In certain aspects, the Fc region of these antibodies is altered to comprise one Asn-X-Thr/Ser triplet located in the same position on both chains of the Fc region. In certain aspects of this embodiment, the Fc region is altered to comprise two Asn-X-Thr/Ser triplets located in the same positions on both chains of the Fc region. In certain aspects of this embodiment, the Fc region is altered to comprise three Asn-X-Thr/Ser triplets located in the same positions on both chains of the Fc region.

In an second embodiment of the method, the invention is drawn to a method for altering the binding affinity of an antibody for an FcγR comprising selecting an antibody having a human IgG Fc region, replacing one or more triplets of three contiguous amino acids on one or both chains of the Fc region by an Asn-X-Thr/Ser triplet, wherein the triplets are independently located such that the Asn of the triplet is at one or more of positions 217-235 and 287-292, wherein the positions correspond to the amino acid sequence of the human IgG1 heavy chain, wherein each X is any amino acid except proline, and producing the antibody under conditions where the Asn residues of the triplets are glycosylated.

In certain aspects, the Fc region of these antibodies is altered to comprise one Asn-X-Thr/Ser triplet located in the same position on both chains of the Fc region. In certain aspects of this embodiment, the Fc region is altered to comprise two Asn-X-Thr/Ser triplets located in the same positions on both chains of the Fc region. In certain aspects of this embodiment, the Fc region is altered to comprise three Asn-X-Thr/Ser triplets located in the same positions on both chains of the Fc region.

In certain aspects, the Fc region of these antibodies is altered to comprise two Asn-X-Thr/Ser triplets located in the same positions on both chains of the Fc region, wherein one of the triplets is located such that the Asn of the triplet is at one of positions 217-235 and wherein the other triplet is located such that the Asn of the triplet is at one of positions 287-292, wherein the positions correspond to the amino acid sequence of the human IgG1 heavy chain. In exemplary aspects, one of the triplets is located such that the Asn of the triplet is at position 226 and the other triplet is located such that the Asn of the triplet is at position 290

In a third embodiment of the method, the invention is drawn to a method for altering the binding affinity of an antibody for an FcγR comprising selecting an antibody having a human IgG Fc region, replacing amino acids corresponding to amino acids 226-228 of human IgG1 of one or both chains of the Fc region with an Asn-X-Thr/Ser triplet wherein each X is any amino acid except proline, and producing the antibody under conditions where Asn residues present at position 226 are glycosylated. As described herein, such an antibody variant may be termed an Fc-226$^{hg}$ antibody variant.

In a fourth embodiment of the method, the invention is drawn to a method for altering the binding affinity of an antibody for an FcγR comprising selecting an antibody having a human IgG Fc region, replacing amino acids corresponding to amino acids 290-292 of human IgG1 of one or both chains of the Fc region with an Asn-X-Thr/Ser triplet wherein each X is any amino acid except proline, and producing the antibody under conditions where Asn residues present at position 290 are glycosylated. As described herein, such an antibody variant may be termed an Fc-290$^{hg}$ antibody variant.

In a fifth embodiment of the method, the invention is drawn to a method for altering the binding affinity of an antibody for an FcγR comprising selecting an antibody having a human IgG Fc region, replacing amino acids corresponding to amino acids 226-228 of human IgG1 of one or both chains of the Fc region with an Asn-X-Thr/Ser triplet, replacing amino acids corresponding to amino acids 290-292 of human IgG1 of one or both chains of the Fc region with an Asn-X-Thr/Ser triplet, wherein each X is any amino acid except proline, and producing the antibody under conditions where Asn residues present at positions 226 and 290 are glycosylated. As described herein, such an antibody variant may be termed an Fc-226$^{hg}$/290$^{hg}$ antibody variant.

In a sixth embodiment of the method, the invention is drawn to a method for altering the binding affinity of an antibody for an FcγR comprising selecting an antibody having a human IgG Fc region, replacing amino acids corresponding to amino acids 226-228 of human IgG1 of one or both chains of the Fc region with an Asn-X-Thr/Ser triplet, replacing amino acids corresponding to amino acids 290-292 of human IgG1 of one or both chains of the Fc region with an Asn-X-Thr/Ser triplet, wherein each X is any amino acid except proline, making a S298A amino acid replacement in one or both of the heavy chains, wherein the location of the replacement corresponds to the amino acid sequence of human IgG1, and producing the antibody under conditions where Asn residues present at positions 226 and 290 are glycosylated. As described herein, such an antibody variant may be termed an Fc-226$^{hg}$/290$^{hg}$/S298A antibody variant.

In each of these embodiments of the method, the method may further comprise making one or more additional amino acid replacements selected from the group consisting of S298A, E333A, and K334A, each independently on one or both of the chains of the Fc region, wherein the location of the replacement corresponds to the amino acid sequence of human IgG1.

In each of these embodiments of the method, the method may further comprise making one or more additional amino acid replacements selected from the group consisting of S239D, I332E, and A330L, each independently on one or both of the chains of the Fc region, wherein the location of the replacement corresponds to the amino acid sequence of human IgG1.

In each of these embodiments of the method, the method may further comprise making a G236A amino acid replacement in one or both chains of the Fc region, wherein the location of the replacement corresponds to the amino acid sequence of human IgG1.

In each of these embodiments of the method, the method may further comprise making a S298A amino acid replacement in one or both chains of the Fc region, wherein the location of the replacement corresponds to the amino acid sequence of human IgG1.

In each of the embodiments of the method, the FcγR is selected from the group consisting of FcγRI (CD64), FcγRIIA (CD32), FcγRIIB (CD32), FcγRIIIA (CD16a), and FcγRIIIB (CD16b).

In each of the methods of the invention, the Asn-X-Thr/Ser triplets may be Asn-Ser-Thr.

In each of the embodiments of the method, it will be clear to the skilled artisan that the binding affinity of the antibody for an FcγR will be increased, decreased, or unchanged. Depending on the desired change, the methods described herein can thus be used to increase the binding affinity of the antibody for an FcγR or can be used to decrease the binding affinity of the antibody for an FcγR. The increase or decrease can be a change of about 5, 10, 15, 20, 25, 30, 35, 40, 45, 50, 55, 60, 65, 70, 75, 80, 85, 90, 95-fold, or more, versus the binding affinity of the unmodified antibody.

In each of these embodiments of the method, and as discussed above, the replacements can be made through a number of different means well known to the skilled artisan. For example, cDNA encoding the IgG heavy chain of a selected antibody can be synthesized and cloned into a mammalian expression plasmid (e.g., pcDNA3.3 from Life Technologies). Mutations can then be made to the cDNA sequence using site-directed mutagenesis, for example. Other suitable means for producing the antibody variants include gene synthesis.

Once genes encoding the antibody variants are produced, they can be expressed under conditions where Asn residues are glycosylated, for example, in cell lines that include the means to glycosylate the asparagine residues. For example, genes encoding light and heavy chain sequences can be expressed in mammalian cell lines, such as CHO cells, and HEK293 cells as an example of a human cell line. Glycosylation of asparagine occurs naturally in such cell lines during protein maturation through the Golgi and endoplasmic reticulum. Additional means for producing the hyper-glycosylation that characterizes the antibodies of the invention include those means disclosed in Wang, L X, et al. (Emerging technologies for making glycan-defined glycoproteins. *ACS Chem Biol.* 2012. 7(1): 110-22) and Huang, W, et al. (Chemoenzymatic glycoengineering of intact IgG antibodies for gain of functions. *J Am Chem Soc.* 2012.134 (29):12308-18).

Fc Region Fusion Proteins

The ability of antibodies to bind and activate Fc receptors through their Fc regions has been recognized and utilized in fusion proteins that pair antibody Fc regions with non-antibody proteins (see, e.g., Chiang, M J et al., An Fc domain protein-small molecule conjugate as an enhanced immunomodulator. *J Am Chem Soc.* 2014. 136(9):3370-3). Such Fc region fusion proteins can be produced that exhibit dual activities, with a first activity being the binding, and optional activation or repression, of an Fc receptor and the second activity being one specifically selected for the fusion protein and imparted by the non-Fc region portion of the protein. Examples of second activities include, but are not limited to, binding, and optionally activating or repressing, a different receptor (both Fc receptors and non-Fc receptors), and inducing a desired cellular activity or effect on a cell. As an example, the such fusion proteins include those having an Fc region domain on one part of the protein (and thus the ability to bind an Fc receptor) and a cytotoxic domain on the other part of the protein (that induced cellular death upon endocytosis).

The present invention includes Fc region fusion proteins wherein the Fc region is hyper-glycosylated in the same manner as the antibodies described herein. As with the antibodies of the invention, in these fusion proteins the additional glycosylation is positioned on asparagine residues within the Fc region. Because the IgG Fc region only contains one asparagine thought to play a role in Fc-FcγR binding (at position 297), the Fc region fusion proteins of the invention are modified to include one or more additional asparagine residues in the Fc region of the protein. The invention includes such Fc region fusion proteins wherein the one or more additional asparagine residues are glycosylated, partially glycosylated or unglycosylated. Suitable positions for the additional asparagines include one or more of positions 217-235 and 287-292, corresponding to the IgG1 heavy chain amino acid sequence, numbered from the amino terminus of the polypeptide sequence. Exemplary positions include 226 and 290.

All references herein to antibodies, polynucleotide molecules, vectors, host cells, and methods of making the antibodies of the invention apply equally to the Fc region fusion proteins of the invention. Thus, the Fc region fusion proteins can comprise the same Asn-X-Thr/Ser triplets and the same glycosylated Asn residues as the antibodies described herein. The Fc region fusion proteins can also be produced in the same manner as the antibodies described herein.

III. Example I

Genetic Engineering

Hyper-glycosylated human IgG1 Fc variants, such as Fc-226$^{hg}$, Fc290$^{hg}$ and Fc-226$^{hg}$/290$^{hg}$, were generated by site-directed mutagenesis in the pcDNA 3.1 vector (Life Technologies, Grand Island, N.Y.) containing the sequence of wild-type IgG1 Fc (SEQ ID NO: 1). To create the new glycosylation sites, sets of three amino acid residues (CPP; KPR; both CPP and KPR) were mutated in the positions shown in bold underlining in the wild-type IgG Fc amino acid sequence (SEQ ID NO:2) to the consensus glycosylation sequence Asn-Ser-Thr (NST) (DNA sequence: AAGAGCACG), resulting in Fc-226$^{hg}$ (SEQ ID NO:3), Fc290$^{hg}$ (SEQ ID NO:4) and Fc-226$^{hg}$/290$^{hg}$ (SEQ ID NO:5). Two residues following the Asn were included in order to provide the full consensus sequence for N-linked glycosylation.

```
Fc-WT DNA sequence (SEQ ID NO: 1):
ATGGAGACAGACACACTCCTGCTATGGGTACTGCTGCTCTGGGTTCCAGG

TTCCACTGGTGAGCCCAAATCTTGTGACAAAACTCACACATGCCCACCGT

GCCCAGCACCTGAACTCCTGGGGGGACCGTCAGTCTTCCTCTTCCCCCCA

AAACCCAAGGACACCCTCATGATCTCCCGGACCCCTGAGGTCACATGCGT
```

-continued

```
GGTGGTGGACGTGAGCCACGAAGACCCTGAGGTCAAGTTCAACTGGTACG

TGGACGGCGTGGAGGTGCATAATGCCAAGACAAAGCCGCGGGAGGAGCAG

TACAACAGCACGTACCGTGTGGTCAGCGTCCTCACCGTCCTGCACCAGGA

CTGGCTGAATGGCAAGGAGTACAAGTGCAAGGTCTCCAACAAAGCCCTCC

CAGCCCCCATCGAGAAAACCATCTCCAAAGCCAAAGGGCAGCCCCGAGAA

CCACAGGTGTACACCCTGCCCCCATCCCGGGAGGAGATGACCAAGAACCA

GGTCAGCCTGACCTGCCTGGTCAAAGGCTTCTATCCCAGCGACATCGCCG

TGGAGTGGGAGAGCAATGGGCAGCCGGAGAACAACTACAAGACCACGCCT

CCCGTGCTGGACTCCGACGGCTCCTTCTTCCTCTATAGCAAGCTCACCGT

GGACAAGAGCAGGTGGCAGCAGGGGAACGTCTTCTCATGCTCCGTGATGC

ATGAGGCTCTGCACAACCACTACACGCAGAAGAGCCTCTCCCTGTCCCCG

GGTAAATGATAA
```

Fc-WT protein sequence (SEQ ID NO: 2):
*METDTLLLWVLLLWVPGST*GEPKSCDKTHTCPPCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

IgG1 Fc variant Fc-226$^{hg}$ (SEQ ID NO: 3):
*METDTLLLWVLLLWVPGST*GEPKSCDKTHTNSTCPAPELLGGPSVFLFPP

KPKDTLMISRTPEVTCVVVDVSHEDPEVKFNWYVDGVEVHNAKTKPREEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

IgG1 Fc variant Fc-290$^{hg}$ (SEQ ID NO: 4):
*METDTLLLWVLLLWVPGST*GEPKSCDKTHTCPPCPAPELLGGPSVFLFPP

KPKDTLMISRTPEVTCVVVDVSHEDPEVKFNWYVDGVEVHNAKTNSTEEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

IgG1 Fc variant Fc-226$^{hg}$/290$^{hg}$ (SEQ ID NO: 5):
*METDTLLLWVLLLWVPGST*GEPKSCDKTHTNSTCPAPELLGGPSVFLFPP

KPKDTLMISRTPEVTCVVVDVSHEDPEVKFNWYVDGVEVHNAKTNSTEEQ

YNSTYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

The leader peptide is shown in italicized underlining in SEQ ID NOs:2-5 and the predicted cleavage site is STG-EP, with the mature protein beginning with residues EP. The variants Fc-226$^{hg}$/290$^{hg}$/S298A/E333A/K334A (SEQ ID NO:6) and Fc-226$^{hg}$/290$^{hg}$/S298A (SEQ ID NO:7) were generated by site-directed mutagenesis in the pcDNA 3.1 Fc-226$^{hg}$/290$^{hg}$ construct. All site-directed mutations were generated using a QuikChange site-directed mutagenesis kit (Agilent).

IgG1 Fc variant Fc-226$^{hg}$/290$^{hg}$/S298A/E333A/K334A (SEQ ID NO: 6):
*METDTLLLWVLLLWVPGST*GEPKSCDKTHTNSTCPAPELLGGPSVFLFPP

KPKDTLMISRTPEVTCVVVDVSHEDPEVKFNWYVDGVEVHNAKTNSTEEQ

YNATYRVVSVLTVLHQDWLNGKEYKCKVSNKALPAPIAATISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

IgG1 Fc variant Fc-226$^{hg}$/290$^{hg}$/S298A (SEQ ID NO: 7):
*METDTLLLWVLLLWVPGST*GEPKSCDKTHTNSTCPAPELLGGPSVFLFPP

KPKDTLMISRTPEVTCVVVDVSHEDPEVKFNWYVDGVEVHNAKTNSTEEQ

YNATYRVVSVLTVLHQDWLNGKEYKCKVSNKALPAPIEKTISKAKGQPRE

PQVYTLPPSREEMTKNQVSLTCLVKGFYPSDIAVEWESNGQPENNYKTTP

PVLDSDGSFFLYSKLTVDKSRWQQGNVFSCSVMHEALHNHYTQKSLSLSP

GK

Protein Expression, Purification and Characterization

Wild type and hyper-glycosylated IgG1 Fc variants were produced in Chinese Hamster Ovary (CHO)-K1 cells. The CHO cells were transiently transfected with the pcDNA3.1 plasmid (13.8 μg/10 mL F12 medium) containing the respective Fc variant gene, using Lipofectamine (Invitrogen) as a transfection reagent following the manufacturer's protocol. After transfection, kifunensine was added to the medium to a final concentration of 2 μg/mL. The culture supernatant was collected 4 days after transfection, dialyzed overnight against 20 mM phosphate buffer and applied to a protein A column (GE Healthcare), eluted in 100 mM citrate, pH 3.5 and immediately neutralized with 1 M Tris-Cl, pH 9. Elution fractions were pooled and further purified by size exclusion chromatography in PBS buffer. The wild-type and hyper-glycosylated Fc variants Fc-271$^{hg}$ and Fc-331$^{hg}$ (two hyper-glycosylated Fc mutants that did not exhibit desired FcγR binding properties) were characterized by mass spectrometry. The glycan profiles for wild-type Fc, Fc-271$^{hg}$ and Fc-331$^{hg}$ were:

WT: 90% Man$_9$GlcNAc$_2$, 10% Man$_6$GlcNAc$_2$

Fc-271$^{hg}$: 80% Man$_9$GlcNAc$_2$, 10% Man$_6$GlcNAc$_2$, 10% mixed fucosylated complex-type Fc-331$^{hg}$: 75% Man$_9$GlcNAc$_2$, 15% Man$_6$GlcNAc$_2$, 10% mixed fucosylated complex-type FcγRs were prepared having a His-tag fused to their C-termini by transient expression in HEK293T using polyethylenimine (PEI; Polysciences, Inc.) as a transfection reagent. The FcγRs included (i) FcγRIIIA having a Phe residue at polymorphic site 158 (FcγRIIIA-158F), (ii) FcγRIIIA having a Val residue at polymorphic site 158 (FcγRIIIA-158V), (iii) FcγRIIA, and (iv) FcγRIIB. The culture supernatants from transfected HEK293T cells were collected 4 days after transfection, dialyzed overnight against 50 mM phosphate buffer pH 7.5, 500 mM NaCl and purified using a Ni$^{2+}$-NTA resin (Thermo Scientific) column.

The Fcγ receptors were eluted using 75-100 mM imidazole and further purify by size exclusion chromatography in PBS buffer.

Protein-Protein Interaction Analysis

The binding affinities of the hyper-glycosylated Fc variants described herein and wild type IgG1 Fc for the inhibitory FcγRIIB and activating FcγRIIA and FcγRIIIA receptors were measured by surface plasmon resonance (SPR) analysis. All experiments were performed using a Biacore T100 instrument (GE Healthcare). Protein A (Sigma-Aldrich) (0.1 mg/mL, 10 mM sodium acetate, pH 4.5) was immobilized at a density of 1000 response units (RU) in flow cells 1 and 2 of a CM5 sensor chip via standard amine-coupling procedure according to the manufacturer's instructions (GE Healthcare), using HBS-X buffer (10 mM HEPES, 150 mM NaCl, 0.05% Tween 20) as the running buffer and a flow rate of 5 μL/min. Flow cell 1 was used as negative control, while flow cell 2 was used to capture wild type or hyper-glycosylated Fc variants in PBS at a density of 100-150 RU. Single cycle kinetics experiments were conducted by injecting increasing concentrations of FcγRIIIA-158F (0.01-0.2 μM), FcγRIIIA-158V (0.006-0.1 μM), FcγRIIB (1.7-150 μM) and FcγRIIA (0.625-10 μM) in running buffer over the Protein A-coated and Fc-captured sensor chip flow cells for 60 s per injection and allowed to dissociate for 300 s at a flow rate of 30 μL/min. Between experiments, the sensor chip surface was regenerated by 2 injections of 15 μL each of 20 mM HC1. Experimental data were corrected for instrument and bulk artifacts by referencing to a control sensor chip surface using Biacore T100 evaluation software 2.0.3 (GE Healthcare). Kinetic parameters of binding were determined using the same software and a 1:1 Langmuir binding model for all FcγRIIIA-158V interactions. Due to extremely fast dissociation rates, kinetic parameters of binding to FcγRIIIA-158F, FcγRIIA and FcγRIIB could not be accurately determined and, thus, the affinity constants, $K_D$s, were determined by steady-state analysis.

The binding affinities of the following hyper-glycosylated IgG Fc variants to FcγRIIIA-158F, FcγRIIIA-158V, FcγRIIB and FcγRIIA were measured: wild-type Fc, Fc-226$^{hg}$, Fc-236$^{hg}$, Fc-267$^{hg}$, Fc-271$^{hg}$, Fc-286$^{hg}$, Fc-290$^{hg}$, Fc-294$^{hg}$, Fc-322$^{hg}$ (protein did not express), Fc-325$^{hg}$, Fc-329$^{hg}$, Fc-330$^{hg}$, Fc-331$^{hg}$, Fc-226$^{hg}$/290$^{hg}$, Fc-E333A/K334A, Fc-S298A, Fc-S298A/E333A/K34A, Fc-226$^{hg}$/290$^{hg}$/S298A/E333A/K334A, Fc-226$^{hg}$/290$^{hg}$/E333A/K334A, and Fc-226$^{hg}$/290$^{hg}$/S298A. The presence of the extra glycan was validated by SDS-PAGE gel (data not shown) as a band shift to a higher molecular weight than the wild type Fc due to the additional engineered glycan in the Fc structure. Fc-267$^{hg}$, Fc-271$^{hg}$, Fc-286$^{hg}$, Fc-294$^{hg}$, Fc-325$^{hg}$, Fc-329$^{hg}$, Fc-330$^{hg}$ and Fc-331$^{hg}$ exhibited no or drastically reduced binding to both activating and the inhibitory Fcγ receptors. Fc-236$^{hg}$ exhibited indistinguishable binding affinities to the Fcγ receptors as did wild type Fc.

Figure 3:
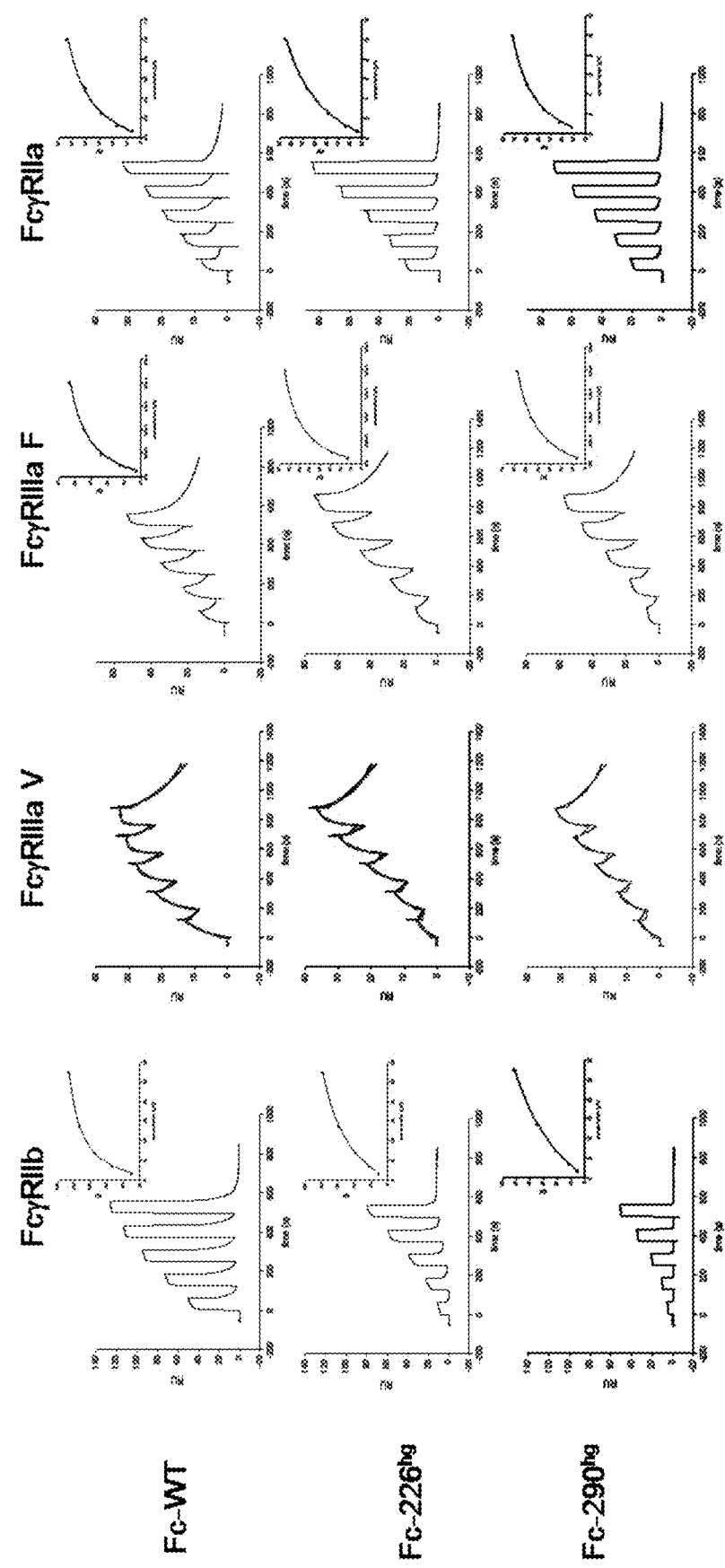
FIG. 3 provides SPR sensorgrams (first, third, and fourth columns) of wild type and singly hyper-glycosylated IgG1 Fcs at different concentrations of Fcγ receptors. In the second column are sensorgrams fitted to a 1:1 Langmuir binding model. Inserts: equilibrium response as a function of hyper-glycosylated Fc concentration.
Figure 4:
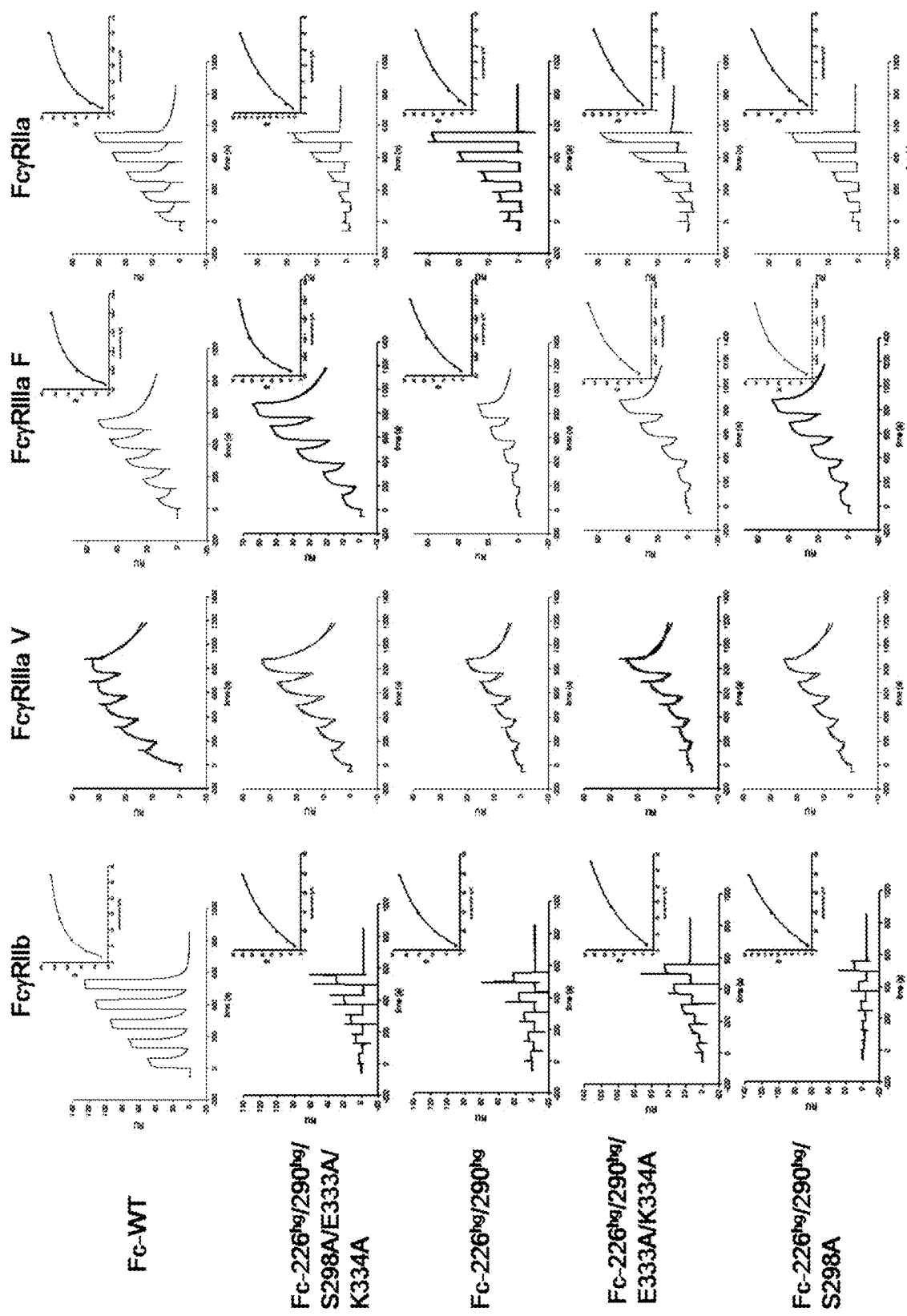
FIG. 4 provides SPR sensorgrams (first, third, and fourth columns) of doubly hyper-glycosylated IgG1 Fc mutants at different concentrations of Fcγ receptors. In the second column are sensorgrams fitted to a 1:1 Langmuir binding model. Inserts: equilibrium response as a function of hyper-glycosylated Fc concentration.

Fc-226$^{hg}$ and Fc-290$^{hg}$ both exhibited 10-fold decreased binding to FcγRIIB with ~6-fold decreased binding to FcγRIIIA and ~4-fold decreased binding to FcγRIIA (FIG. 3). Moreover, the optimized IgG Fc variant Fc-226$^{hg}$/290$^{hg}$/S298A exhibited, relative to wild type IgG Fc, 60-fold reduced binding to the inhibitory FcγRIIB, with only 6-fold and 10-fold reduced binding to the activating receptors FcγRIIIA and FcγRIIA, respectively (FIG. 4). Detailed data for each hyper-glycosylated Fc variant and for the amino acid variations previously found by others to reduce IgG Fc binding to the inhibitory FcγR and/or increase binding to activating FcγRs to confirm the decreased binding it is due the extra-glycan are described in Tables 1 and 2.

TABLE 1

Hyper-glycosylated Fc binding affinity (KD) to activating and inhibitory FcγRs

| Mutant | FcγRIIB ($K_D$ = μM) | FcγRIIIA-158V ($K_D$ = nM) | FcγRIIIA-158F ($K_D$ = nM) | FcγRIIA ($K_D$ = μM) |
|---|---|---|---|---|
| Fc-WT | 1.7 ± 0.5 (5) | 3.2 ± 0.5 (3) | 12.8 ± 0.8 (5) | 1.2 ± 0.1 (2) |
| Fc-226$^{hg}$ | 17.3 ± 1.2 (5) | 19.2 ± 1 (2) | 71.8 ± 6.3 (2) | 5.6 ± 0.9 (3) |
| Fc-290$^{hg}$ | 18.8 ± 3.5 (5) | 20.8 ± 16.4 (2) | 66.1 ± 18.4 (2) | 3.2 ± 0.2 (3) |
| Fc-226$^{hg}$/290$^{hg}$ | 51.2 ± 5.1 (3) | 27.5 ± 2.3 (2) | 159.7 ± 12.3 (3) | 9.1 ± 0.8 (2) |
| Fc-E333A/K334A | 3.3 ± 0.7 (4) | 1.7 ± 0.4 (2) | 3.3 ± 1.1 (3) | 2.0 ± 0.12 (2) |
| Fc-S298A | 6.9 ± 2.6 (4) | 1.5 ± 0.4 (2) | 24.5 ± 8.5 (3) | 5.1 ± 1.2 (2) |
| Fc-S298A/E333A/K334A | 7.1 ± 1.5 (4) | 2.1 ± 0.9 (2) | 48.8 ± 23.7 (2) | 5.0 < 0.1 (2) |
| Fc-226$^{hg}$/290$^{hg}$/S298A/E333A/K334A | 64.2 ± 5 (3) | 15.5 ± 2 (2) | 50.1 ± 5.2 (3) | 12.8 ± 6.8 (2) |
| Fc-226$^{hg}$/290$^{hg}$/E333A/K334A | 20.8 ± 2.7 (5) | 57.0 ± 13.3 (2) | 151.0 ± 26.7 (3) | 13.4 ± 3.3 (2) |
| Fc-226$^{hg}$/290$^{hg}$/S298A | 103.5 ± 32.7 (2) | 20.2 ± 4.5 (3) | 87.8 ± 7.7 (3) | 12.8 ± 3.1 (2) |

( ) = Number of replicates

TABLE 2

Hyper-glycosylated Fc fold decrease in binding (Fc-variant $K_D$/Fc-WT $K_D$) to activating and inhibitory FcγRs

| Mutant | FcγRIIB | FcγRIIIA-158V | FcγRIIIA-158F | FcγRIIA |
|---|---|---|---|---|
| Fc-WT | 1 | 1 | 1 | 1 |
| Fc-226$^{hg}$ | 10.2 | 6.1 | 5.6 | 4.7 |
| Fc-290$^{hg}$ | 11.1 | 6.5 | 5.2 | 2.7 |
| Fc-226$^{hg}$/290$^{hg}$ | 30.1 | 8.6 | 12.4 | 7.6 |
| Fc-E333A/K334A | 1.9 | 0.5 | 0.2 | 1.7 |
| Fc-S298A | 4.0 | 0.5 | 1.9 | 4.2 |
| Fc-S298A/E333A/K334A | 4.2 | 0.6 | 3.8 | 4.2 |
| Fc-226$^{hg}$/290$^{hg}$/S298A/E333A/K334A | 37.8 | 4.8 | 3.9 | 10.7 |
| Fc-226$^{hg}$/290$^{hg}$/E333A/K334A | 12.2 | 17.8 | 11.8 | 11.2 |
| Fc-226$^{hg}$/290$^{hg}$/S298A | 60.9 | 6.3 | 6.9 | 10.7 |

IV. Example II

Production and Validation of Hyper-Glycosylated Rituximab and Trastuzamab

Hyper-glycosylated versions of the therapeutic antibodies Rituximab and Trastuzamab will be produced and tested. cDNA encoding the IgG heavy and light chains of both Rituximab and Trastuzamab will be synthesized and cloned into the mammalian expression plasmid pcDNA3.3 (Life Technologies). To create hyper-glycosylated expression plasmids for these mAbs, the 226$^{hg}$/290$^{hg}$/S298A mutations will be incorporate using site-directed mutagenesis. Both wild-type and hyper-glycosylated modified versions of Rituximab and Trastuzamab will be expressed in HEK293T cells by transfecting these cells with the prepared expression plasmids using polyethylenimine. Antibodies secreted into the medium will be collected 3-5 days post-transfection and purified by Protein A affinity chromatography as described above. Purified antibodies will be validated by measuring their FcγR binding capacities by surface plasmon resonance (SPR) analysis as described above.

Acute Tolerability Study (MTD)

Tolerability (Max dose/MTD) of the hyper-glycosylated Rituximab and Trastuzamab will be tested (4 arms). Escalating doses (0, 10, 25, 50, and 100 mg/kg) will be administered to Balb/C mice (n=5/dose) on days 1 and 7. Animals will be monitored for adverse effects for 28 days. Endpoints used to evaluate the onset of adverse effects will include clinical observations and body weight. At the end of the study, animals will be euthanized and biological specimens (serum/plasma and tissues) archived for future studies.

Pharmacokinetic Study

Pharmacokinetics of the hyper-glycosylated Rituximab and Trastuzamab will be compared and a dosing regimen (route/dose/schedule) will be verified via efficacy studies. Balb/C mice (n=3/time point) will be euthanized 0, 6, 24, 48, 72, and 96 hrs after a single IV dose of drug labeled with a near-infrared dye. Specimens (blood/tissues) will be examined on an IVIS Lumina XR Imaging System, drug levels reported as the relative infrared intensity. Specimens will be archived for toxicology analysis (fixed tissue). Plasma pharmacokinetic parameters include areas under the plasma concentration-time curve, concentration ($C_{max}$) and time to $C_{max}$ will be determined.

Efficacy Study

The efficacy of Trastuzumab will be compared to the hyper-glycosylated version of the antibody (2 arms) in the treatment of breast cancer. Anti-breast cancer activity will be determined in a xenograft model (Clynes et al., (2002) Nat Med 6:443-446). A pilot study will be performed to insure the model exhibits breast cancer activity that is amenable to Trastuzamab therapy (n=10). For the efficacy study, mice (n=10/arm) will receive control or experimental formulations for 6 weeks with the optimal dosing regimen identified as described above. Tumor size will be recorded every 2 days and tumor response will be expressed as the mean tumor proliferation rate+/–the SEM, i.e. tumor volume, (V=½ab$^2$) on days 7, 14, 21, 28, 35, 42 divided by the tumor volume at day 0. Overall health status will be assessed using a scoring matrix that includes: behavioral changes; amputation/posture, activity, coat, facial expression, neurological & respiratory problems, systemic toxicity (body weight). At the end of the study, animals will be euthanized, tumor sizes recorded, internal organs examined (gross pathology), and biological specimens (plasma, liver, kidney, brain, and tumor) harvested/archived.

While the invention has been described with reference to certain particular embodiments thereof, those skilled in the art will appreciate that various modifications may be made without departing from the spirit and scope of the invention. The scope of the appended claims is not to be limited to the specific embodiments described.

All patents and publications mentioned in this specification are indicative of the level of skill of those skilled in the art to which the invention pertains. Each cited patent and publication is incorporated herein by reference in its entirety.

What is claimed is:

1. An antibody comprising a human IgG Fc region wherein one or more triplets of three contiguous amino acids on one or both chains of the Fc region is replaced by an Asn-X-Thr/Ser triplet, wherein the triplets are independently located such that the Asn of the triplet is at one or more of positions 226 and 290, wherein the positions correspond to the amino acid sequence of human IgG1 heavy chain using Eu numbering system, wherein each X is any amino acid except proline, and wherein the Asn of the triplet is glycosylated, partially glycosylated or unglycosylated.

2. The antibody according to claim 1, wherein the Fc region is altered to comprise two Asn-X-Thr/Ser triplets located in the same positions on both chains of the Fc region, wherein one of the triplets is located such that the Asn of the triplet is at position 226 and wherein the other triplet is located such that the Asn of the triplet is at position 290.

3. The antibody of claim 1, wherein one or both chains of the Fc region have Asn-X-Thr/Ser triplet replacements at positions 226-228.

4. The antibody of claim 3, wherein both chains of the Fc region have the noted Asn-X-Thr/Ser triplets.

5. The antibody of claim 3, wherein the antibody further comprises one or more additional amino acid replacements selected from the group consisting of S298A, E333A, and K334A, each independently on one or both chains of the Fc region.

6. The antibody of claim 3, wherein the antibody further comprises one or more additional amino acid replacements selected from the group consisting of S239D, I332E, and A330L, each independently on one or both chains of the Fc region.

7. The antibody of claim 3, wherein the antibody further comprises a G236A amino acid replacement on one or both chains of the Fc region.

8. The antibody of claim 3, wherein the Asn-X-Thr/Ser triplets are Asn-Ser-Thr.

9. The antibody of claim 3, wherein the Asn of the triplet is glycosylated.

10. The antibody of claim 3, wherein the triplet is Asn-Ser-Thr.

11. The antibody of claim 10, wherein the antibody further comprises one or more additional amino acid replacements selected from the group consisting of S298A, E333A, and K334A, each independently on one or both chains of the Fc region.

12. The antibody of claim 10, wherein the antibody further comprises one or more additional amino acid replacements selected from the group consisting of S239D, I332E, and A330L, each independently on one or both chains of the Fc region.

13. The antibody of claim 10, wherein the antibody further comprises a G236A amino acid replacement on one or both of the chains of the Fc region.

14. The antibody of claim 10, wherein both chains of the Fc region have the Asn-Ser-Thr replacements.

15. The antibody of claim 10, wherein the Asn of the triplet is glycosylated.

16. The antibody of claim 10, wherein both chains of the Fc region have Asn-Ser-Thr replacements at positions 226-228, both chains of the Fc region have Asn-Ser-Thr replacements at positions 290-292, wherein Asn residues present at positions 226 and 290 are glycosylated, and wherein both heavy chains have a S298A amino acid replacement corresponding to the amino acid sequence of human IgG1.

* * * * *

SEQUENCE LISTING

```
<160> NUMBER OF SEQ ID NOS: 11

<210> SEQ ID NO 1
<211> LENGTH: 762
<212> TYPE: DNA
<213> ORGANISM: Homo sapiens

<400> SEQUENCE: 1
atggagacag acacactcct gctatgggta ctgctgctct gggttccagg ttccactggt      60
gagcccaaat cttgtgacaa aactcacaca tgcccaccgt gcccagcacc tgaactcctg     120
gggggaccgt cagtcttcct cttccccca aaacccaagg acaccctcat gatctcccgg      180
acccctgagg tcacatgcgt ggtggtggac gtgagccacg aagaccctga ggtcaagttc     240
aactggtacg tggacggcgt ggaggtgcat aatgccaaga caaagccgcg ggaggagcag     300
tacaacagca cgtaccgtgt ggtcagcgtc ctcaccgtcc tgcaccagga ctggctgaat     360
ggcaaggagt acaagtgcaa ggtctccaac aaagccctcc cagcccccat cgagaaaacc     420
atctccaaag ccaaagggca gccccgagaa ccacaggtgt acaccctgcc cccatcccgg     480
gaggagatga ccaagaacca ggtcagcctg acctgcctgg tcaaaggctt ctatcccagc     540
gacatcgccg tggagtggga gagcaatggg cagccggaga caactacaa gaccacgcct     600 cccgtgctgg actccgacgg ctccttcttc ctctatagca agctcaccgt ggacaagagc     660
aggtggcagc aggggaacgt cttctcatgc tccgtgatgc atgaggctct gcacaaccac     720
tacacgcaga agagcctctc cctgtccccg ggtaaatgat aa                        762
```

```
<210> SEQ ID NO 2
<211> LENGTH: 252
<212> TYPE: PRT
<213> ORGANISM: Homo sapiens

<400> SEQUENCE: 2

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Lys Pro
                85                  90                  95

Arg Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
    130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 3
<211> LENGTH: 252
<212> TYPE: PRT
<213> ORGANISM: Artificial Sequence
<220> FEATURE:
<223> OTHER INFORMATION: Chemically-synthesized IgG1 Fc variant

<400> SEQUENCE: 3

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Asn Ser
            20                  25                  30

Thr Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
```

```
            65                  70                  75                  80
Asn Trp Tyr Val Asp Gly Val Glu Val His Asn Ala Lys Thr Lys Pro
                    85                  90                  95

Arg Glu Glu Gln Tyr Asn Ser Thr Tyr Arg Val Val Ser Val Leu Thr
                    100                 105                 110

Val Leu His Gln Asp Trp Leu Asn Gly Lys Glu Tyr Lys Cys Lys Val
                    115                 120                 125

Ser Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                    165                 170                 175

Phe Tyr Pro Ser Asp Ile Ala Val Glu Trp Glu Ser Asn Gly Gln Pro
                    180                 185                 190

Glu Asn Asn Tyr Lys Thr Thr Pro Pro Val Leu Asp Ser Asp Gly Ser
                    195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                    245                 250

<210> SEQ ID NO 4
<211> LENGTH: 252
<212> TYPE: PRT
<213> ORGANISM: Artificial Sequence
<220> FEATURE:
<223> OTHER INFORMATION: Chemically-synthesized IgG1 Fc variant

<400> SEQUENCE: 4

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Cys Pro
            20                  25                  30

Pro Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
    50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Asn Ser
                    85                  90                  95

Thr Glu Glu Gln Tyr Asn Ser Thr Tyr Arg Val Val Ser Val Leu Thr
                    100                 105                 110

Val Leu His Gln Asp Trp Leu Asn Gly Lys Glu Tyr Lys Cys Lys Val
                    115                 120                 125

Ser Asn Lys Ala Leu Pro Ala Pro Ile Glu Lys Thr Ile Ser Lys Ala
            130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                    165                 170                 175

Phe Tyr Pro Ser Asp Ile Ala Val Glu Trp Glu Ser Asn Gly Gln Pro
```

```
                    180                 185                 190
Glu Asn Asn Tyr Lys Thr Thr Pro Pro Val Leu Asp Ser Asp Gly Ser
                195                 200                 205

Phe Phe Leu Tyr Ser Lys Leu Thr Val Asp Lys Ser Arg Trp Gln Gln
            210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 5
<211> LENGTH: 252
<212> TYPE: PRT
<213> ORGANISM: Artificial Sequence
<220> FEATURE:
<223> OTHER INFORMATION: Chemically-synthesized IgG1 Fc variant

<400> SEQUENCE: 5

Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Asn Ser
                20                  25                  30

Thr Cys Pro Ala Pro Glu Leu Leu Gly Gly Pro Ser Val Phe Leu Phe
            35                  40                  45

Pro Pro Lys Pro Lys Asp Thr Leu Met Ile Ser Arg Thr Pro Glu Val
        50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Asn Ser
                85                  90                  95

Thr Glu Glu Gln Tyr Asn Ser Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Glu Lys Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
    210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 6
<211> LENGTH: 252
<212> TYPE: PRT
<213> ORGANISM: Artificial Sequence
<220> FEATURE:
<223> OTHER INFORMATION: Chemically-synthesized IgG1 Fc variant
```

<400> SEQUENCE: 6

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Asn Ser
            20                  25                  30

Thr Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Asn Ser
                85                  90                  95

Thr Glu Glu Gln Tyr Asn Ala Thr Tyr Arg Val Val Ser Val Leu Thr
            100                 105                 110

Val Leu His Gln Asp Trp Leu Asn Gly Lys Glu Tyr Lys Cys Lys Val
        115                 120                 125

Ser Asn Lys Ala Leu Pro Ala Pro Ile Ala Ala Thr Ile Ser Lys Ala
130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250
```

<210> SEQ ID NO 7
<211> LENGTH: 252
<212> TYPE: PRT
<213> ORGANISM: Artificial Sequence
<220> FEATURE:
<223> OTHER INFORMATION: Chemically-synthesized IgG1 Fc variant

<400> SEQUENCE: 7

```
Met Glu Thr Asp Thr Leu Leu Leu Trp Val Leu Leu Leu Trp Val Pro
1               5                   10                  15

Gly Ser Thr Gly Glu Pro Lys Ser Cys Asp Lys Thr His Thr Asn Ser
            20                  25                  30

Thr Cys Pro Ala Pro Glu Leu Leu Gly Gly Pro Ser Val Phe Leu Phe
        35                  40                  45

Pro Pro Lys Pro Lys Asp Thr Leu Met Ile Ser Arg Thr Pro Glu Val
50                  55                  60

Thr Cys Val Val Val Asp Val Ser His Glu Asp Pro Glu Val Lys Phe
65                  70                  75                  80

Asn Trp Tyr Val Asp Gly Val Glu Val His Asn Ala Lys Thr Asn Ser
                85                  90                  95
```

```
Thr Glu Glu Gln Tyr Asn Ala Thr Tyr Arg Val Val Ser Val Leu Thr
                100                 105                 110

Val Leu His Gln Asp Trp Leu Asn Gly Lys Glu Tyr Lys Cys Lys Val
            115                 120                 125

Ser Asn Lys Ala Leu Pro Ala Pro Ile Glu Lys Thr Ile Ser Lys Ala
        130                 135                 140

Lys Gly Gln Pro Arg Glu Pro Gln Val Tyr Thr Leu Pro Pro Ser Arg
145                 150                 155                 160

Glu Glu Met Thr Lys Asn Gln Val Ser Leu Thr Cys Leu Val Lys Gly
                165                 170                 175

Phe Tyr Pro Ser Asp Ile Ala Val Glu Trp Glu Ser Asn Gly Gln Pro
            180                 185                 190

Glu Asn Asn Tyr Lys Thr Thr Pro Pro Val Leu Asp Ser Asp Gly Ser
        195                 200                 205

Phe Phe Leu Tyr Ser Lys Leu Thr Val Asp Lys Ser Arg Trp Gln Gln
210                 215                 220

Gly Asn Val Phe Ser Cys Ser Val Met His Glu Ala Leu His Asn His
225                 230                 235                 240

Tyr Thr Gln Lys Ser Leu Ser Leu Ser Pro Gly Lys
                245                 250

<210> SEQ ID NO 8
<211> LENGTH: 330
<212> TYPE: PRT
<213> ORGANISM: Homo sapiens

<400> SEQUENCE: 8

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 9
<211> LENGTH: 326
<212> TYPE: PRT
<213> ORGANISM: Homo sapiens

<400> SEQUENCE: 9

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
        115                 120                 125

Thr Leu Met Ile Ser Arg Thr Pro Glu Val Thr Cys Val Val Val Asp
    130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
```

```
                    260                 265                 270
Thr Pro Pro Met Leu Asp Ser Asp Gly Ser Phe Phe Leu Tyr Ser Lys
            275                 280                 285

Leu Thr Val Asp Lys Ser Arg Trp Gln Gln Gly Asn Val Phe Ser Cys
        290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 10
<211> LENGTH: 377
<212> TYPE: PRT
<213> ORGANISM: Homo sapiens

<400> SEQUENCE: 10

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300
```

```
Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375

<210> SEQ ID NO 11
<211> LENGTH: 327
<212> TYPE: PRT
<213> ORGANISM: Homo sapiens

<400> SEQUENCE: 11

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285

Arg Leu Thr Val Asp Lys Ser Arg Trp Gln Glu Gly Asn Val Phe Ser
    290                 295                 300
```

```
Cys Ser Val Met His Glu Ala Leu His Asn His Tyr Thr Gln Lys Ser
305                 310                 315                 320
Leu Ser Leu Ser Leu Gly Lys
                325
```